US011958912B2

(12) United States Patent
Moelleken et al.

(10) Patent No.: US 11,958,912 B2
(45) Date of Patent: Apr. 16, 2024

(54) METHOD FOR DETERMINING THE IN VIVO INTERACTION MODE

(71) Applicant: Hoffmann-La Roche Inc., Little Falls, NJ (US)

(72) Inventors: Joerg Moelleken, Munich (DE); Michael Molhoj, Munich (DE); Christian Gassner, Penzberg (DE); Manuel Endesfelder, Wessling (DE); Joerg-Thomas Regula, Munich (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 677 days.

(21) Appl. No.: 17/062,302

(22) Filed: Oct. 2, 2020

(65) Prior Publication Data

US 2021/0198383 A1  Jul. 1, 2021

Related U.S. Application Data

(63) Continuation of application No. 16/003,475, filed on Jun. 8, 2018, now abandoned, which is a continuation of application No. PCT/EP2016/080292, filed on Dec. 8, 2016.

(30) Foreign Application Priority Data

Dec. 9, 2015 (EP) ..................................... 15198582

(51) Int. Cl.
*G01N 31/00* (2006.01)
*C07K 16/46* (2006.01)
*G01N 33/53* (2006.01)
*G01N 33/536* (2006.01)

(52) U.S. Cl.
CPC .......... *C07K 16/461* (2013.01); *C07K 16/468* (2013.01); *G01N 33/53* (2013.01); *G01N 33/536* (2013.01); *C07K 2317/52* (2013.01); *C07K 2317/55* (2013.01); *C07K 2317/92* (2013.01)

(58) Field of Classification Search
None
See application file for complete search history.

(56) References Cited

FOREIGN PATENT DOCUMENTS

| JP | 2013087087 | | 5/2013 |
|----|---|---|---|
| WO | 95/11298 | A1 | 4/1995 |
| WO | 2006/069403 | A2 | 6/2006 |
| WO | 2009/099728 | A1 | 8/2009 |
| WO | 2015/040125 | A1 | 3/2015 |
| WO | 2015/073580 | A1 | 5/2015 |
| WO | 2015/086549 | A1 | 6/2015 |

OTHER PUBLICATIONS

Moelleken et al. (MABS, 2017, vol. 9, No. 7, pp. 1076-1087) (Year: 2017).*
Bobrovnik et al., "The influence of rigid or flexible linkage between two ligands on the effective affinity and avidity for reversible interactions with bivalent receptors" Journal of Molecular Recognition 20:253-262 (Jun. 24, 2007).
Gassner, C. et al., "Development and validation of a novel SPR-based assay principle for bispecific molecules" J Pharm Biomed Anal 102:144-149 (Jan. 1, 2015).
Inagaki, S., et al., "Antibody Responses of Periodontitis Patients to Gingipains ofPorphyromonas gingivalis" J Periodontol 74(10):1432-1439 (Oct. 1, 2003).
"International Search Report—PCT/EP2016/080292" (w/Written Opinion), pp. 1-18 (dated Feb. 17, 2017).
Kadowaki, T., et al., "Purification and Characterization of a Novel Arginine-specific" J Biol Chem 269(33):21371-21378 (Aug. 19, 1994).
Kikuchi, Y. et al., "Determination of concentration and binding affinity of antibody fragments by use of surface plasmon resonance" J Biosci Bioeng 100(3):311-317 (Sep. 1, 2005).
Lottspeich and Engels Bioanalytik (Spektrum Akademischer Verlag), 2nd edition, Munich::201-214 ( 2006).
Moelleken, J., et al., "GingisKHAN protease cleavage allows a high-throughput antibody to Fab conversion enabling direct functional assessment during lead identification of human monoclonal and bispecific igG1 antibodies" MABS 9(7):1076-1087 (Aug. 14, 2017).
Pack, P. et al., "Tetravalent Miniantibodies with High Avidity Assembling in *Escherlchla coil*" J Mol Biol 246(1):28-34 (Feb. 10, 1995).
Strachan, G., et al., "Binding characteristics of anti-atrazine monoclonal antibodies and their fragments synthesised in bacteria and plants" Biosens Bioelectron 13(6):665-673 (Sep. 15, 1998).
Vincents, B., et al., "Cleavage of IgG1 and IgG3 by gingipain K from Porphyromonas gingivalis may compromise host defense in progressive periodontitis" FASEB J 25(10):3741-3750 (Oct. 1, 2011).
Vincents, B., et al., "Enzymatic characterization of the streptococcal endopeptidase, IdeS, reveals that it is a cysteine protease with strict specificity for IgG cleavage due to exosite binding" Biochemistry 43(49):15540-15549 (Dec. 14, 2004).
Von Pawel-Rammingen, U., et al., "IdeS, a novel streptococcal cysteine proteinase with unique specificity for immunoglobulin G" EMBO J 21(7):1607-1615 (Apr. 2, 2002).

* cited by examiner

*Primary Examiner* — Lisa V Cook
(74) *Attorney, Agent, or Firm* — Lawrence S. Graham

(57) ABSTRACT

Herein is reported a method for determining the binding interaction with a multimeric antigen of an antibody of the human IgG1 subclass that has at least two binding sites specifically binding to the antigen comprising the steps of 1) determining the binding affinity of the antibody for the multimeric antigen, and 2) incubating a mixture comprising the antibody and a polypeptide that is derived from lysine-gingipain of *Porphyromonas gingivalis* under conditions and for a time sufficient to cleave the antibody into Fabs and Fc-region, and determining the binding affinity of the Fabs of the antibody for the multimeric, whereby the binding affinity of the antibody to the multimeric antigen to be affinity-driven if the binding affinity determined in both steps are comparable and to be avidity-driven if the binding affinity determined in both steps are different.

34 Claims, 10 Drawing Sheets

Specification includes a Sequence Listing.

METHOD FOR DETERMINING THE IN VIVO INTERACTION MODE

CROSS-REFERENCE TO RELATED APPLICATIONS

This application is a continuation of U.S. application Ser. No. 16/003,475, filed Jun. 8, 2019, which is a continuation of International Patent Application No. PCT/EP2016/080292, having an international filing date of Dec. 8, 2016, the entire contents of which are incorporated herein by reference, and which claims benefit under 35 U.S.C. § 119 to European Patent Application No. 15198582.7, filed on Dec. 9, 2015.

SEQUENCE LISTING

The instant application contains a Sequence Listing which has been submitted electronically in ASCII format and is hereby incorporated by reference in its entirety. Said ASCII copy, created on Oct. 2, 2020 is named P33255-US_1_Sequence_Listing.txt and is 28,082 bytes in size.

FIELD OF THE INVENTION

The current invention is in the field of immunoassays. Especially herein is reported a method for the selection of a binding assay reflecting the interaction mode, i.e. affinity or avidity, of a therapeutic binder (drug) to each of its targets properly. This is relevant for the selection of a binding assay reflecting the binding strength of a therapeutic binder (drug).

BACKGROUND OF THE INVENTION

The quality of a biopharmaceutical product is of decisive importance in addition to its action. Therefore in addition to a detailed investigation of the modes of action, it is absolutely essential to determine the identity, purity and activity of protein-based drugs in order to use them safely as therapeutic agents.

Monoclonal antibodies (mAbs) can be successfully analyzed by means of various separation and testing techniques.

Papain, a cysteine protease, cleaves peptide bonds relatively non-specifically after arginine (R), lysine (K), glutamic acid (E), histidine (H), glycine (G) and tyrosine (Y). If the incubation period is sufficiently long, the papain digestion leads to a total hydrolysis. However, antibodies can be cleaved relatively selectively in their hinge region by a limited proteolysis (Lottspeich, F., and Engels, J. W., "Bioanalytik Spektrum Akademischer Verlag" Munich 2nd Edition (2006) 201-214). The cleavage occurs on the N-terminal side of the disulfide bridges which connect the two heavy chains together. The disulfide bridges are retained in this process so that three fragments (2 Fab fragments, 1 Fc fragment) are obtained after the digestion. The two N-terminal fragments are referred to as antigen-binding fragments (Fab, antigen-binding fragment), the C-terminal fragment is referred to as the crystalline fragment (Fc, crystallizing fragment). Each Fab fragment is composed of a complete light chain and the amino-terminal half of the heavy chain. The Fc fragment is composed of the two carboxy-terminal halves of the heavy chains which are still linked together by the disulfide bridge.

In recent years different IgG specific proteases have been identified.

In WO 2015/40125 streptococcal erythrogenic toxin B (SpeB) is reported. It is described as a cysteine protease from *Streptococcus pyogenes*, shown to cleave IgG in the hinge region into two stable monomeric Fab fragments and one Fc fragment. It is further reported that SpeB cleaves the hinge region of IgG between positions 238 and 239 according to the Kabat numbering system (positions 225 and 226 according to EU numbering system).

The cysteine endoprotease IdeS (Immunoglobulin degrading enzyme S) from the human pathogen *Streptococcus pyogenes* which is also referred to as Mac-1 or sib-38, is a cysteine protease that specifically cleaves the heavy chain of antibodies of the immunoglobulin G type (IgG). IgG is hitherto the only known substrate of IdeS (Vincents, B., et al., Biochem. 43 (2004) 15540-15549). IdeS consists of 339 amino acids including a signal peptide comprising 29 amino acids (von Pawel-Rammingen, U., et al., EMBO J. 21 (2002) 1607-1615) where an RGD motif is formed by the amino acids 214 to 216. IdeS cleaves human IgG (class G immunoglobulin) in the hinge region between positions 249 and 250 according to the Kabat numbering system (positions 236 and 237 according to EU numbering system) (Gly-Gly), which are contained in the recognition sequence LLGGP. Human IgG2 is cleaved between the amino acids alanine and glycine in the recognition motif PVAGP. Murine antibodies of the IgG2a and IgG3 type are also cleaved (Vincents, B., et al., Biochem. 43 (2004) 15540-15549).

*Porphyromonas gingivalis* is a major pathogenic factor of the progressive periodontal disease (see e.g. Kadowaki, T., et al., J. Biol. Chem. 269 (1994) 21371-21378). Therefrom different enzymes have been isolated, amongst them gingipains, trypsin-like cysteine proteases.

Kikuchi, Y., et al. reported the determination of concentration and binding affinity of antibody fragments by use of surface plasmon resonance (J. Biosci. Bioeng. 100, (2005) 311-317).

In WO 95/11298 a substantially pure Lys-gingipain complex preparation is provided, wherein Lys-gingipain being characterized as having an apparent molecular mass of 105 kDa as estimated by sodium dodecyl sulfate polyacrylamide gel electrophoresis, where sample is prepared without boiling, said Lys-gingipain having amidolytic and proteolytic activity for cleavage after lysine residues and having no amidolytic and/or proteolytic activity for cleavage after arginine residues, wherein the amidolytic and/or proteolytic activity is inhibited by TLCK, cysteine protease group-specific inhibitors including iodoacetamide and iodoacetic acid, wherein the amidolytic and/or proteolytic activity of said Lys-gingipain is not sensitive to inhibition by leupeptin, antipain, trans-epoxysuccinyl-L-leucylamido-(4-guanidino) butane, serine protease group-specific inhibitors including diisopropyl fluoro phosphate and phenyl methyl sulfonyl fluoride, and antibodies specific for the Lys-gingipain protein complex and its catalytic component, methods for preparation.

In WO 2015/086549 is reported the use of a binding assay of a bivalent, bispecific antibody that has the smaller kD value (dissociation constant) for the interaction with its antigen for the immobilization of the bivalent, bispecific antibody to a solid surface for the determination of the biological activity of the bivalent, bispecific antibody.

Inagaki, S., et al. reported about antibody responses of periodontitis patients to gingipains of *Porphyromonas gingivalis* (J. Periodont. 74 (2003) 1432-1439).

SUMMARY OF THE INVENTION

Herein is reported a method for the selection of a (functional) binding immunoassay for a multispecific binder, such as e.g. a bispecific antibody. Functional assessment of bispecific molecules requires consideration of additional aspects as compared to standard antibodies, i.e. the assay format should reflects the in vivo interaction for the individual target and considers the binding sites of the drug. This aspect guides the selection of an immunoassay for determining functionality of the drug and for decision making, e.g. enabling determination of correct binding values, or maximizing the identification of best suitable drugs.

One aspect as reported herein is a method for determining the binding interaction with a multimeric antigen of an antibody of the human IgG1 subclass that has at least two binding sites specifically binding to the antigen comprising the following steps:
1) determining the binding affinity of the antibody for the multimeric antigen,
2) incubating a mixture comprising the antibody and a polypeptide that is derived from lysine-gingipain of *Porphyromonas gingivalis* under conditions and for a time sufficient to cleave the antibody into Fabs and Fc-region, and determining the binding affinity of the Fabs of the antibody for the multimeric antigen, and
determining the binding affinity of the antibody to the multimeric antigen to be affinity-driven if the binding affinity determined in both steps is comparable and to be avidity-driven if the binding affinity determined in both steps is different.

One aspect as reported herein is a method for determining the binding interaction with a multimeric antigen of an antibody of the human IgG1 subclass comprising the following steps:
1) determining the binding affinity of the antibody for the multimeric antigen,
2) incubating a mixture comprising the antibody, the antigen and lysine-gingipain of *Porphyromonas gingivalis* or an enzymatically active fragment thereof at a pH of 7.5 to 8.5, in the presence of a reducing agent, at a temperature of 30° C. to 42° C., for a time of 10 min. to 240 min. to cleave the antibody into Fabs and Fc-region, whereby the concentration of the antibody is higher than the concentration of the antigen, and determining the binding affinity of the Fabs of the antibody for the multimeric antigen, and
determining the binding affinity of the antibody to the multimeric antigen to be affinity-driven if the binding affinity determined in both steps is comparable and to be avidity-driven if the binding affinity determined in both steps is different.

One aspect as reported herein is a method for selecting the assay format for determining the binding interaction of an antibody of the human IgG1 subclass with a multimeric antigen comprising the following steps:
1) determining the binding affinity of the antibody for the multimeric antigen using a surface plasmon resonance method,
2) incubating a mixture comprising the antibody, the antigen and lysine-gingipain of *Porphyromonas gingivalis* or an enzymatically active fragment thereof at a pH of 7.5 to 8.5, in the presence of a reducing agent, at a temperature of 30° C. to 42° C., for a time of 10 min. to 240 min. to cleave the antibody into Fabs and Fc-region, whereby the concentration of the antibody is higher than the concentration of the antigen, and determining the binding affinity of the Fabs of the antibody for their antigen using surface plasmon resonance by directly applying the incubated reaction mixture obtained in the previous step in the surface plasmon resonance method,
whereby the binding affinity of the antibody to the multimeric antigen is i) affinity-driven if the binding affinity determined in both steps is comparable, or ii) avidity-driven if the binding affinity determined in both steps is different,
and
selecting
i) in case of an affinity-driven interaction with a soluble multimeric antigen a solution assay,
ii) in case of an avidity-driven interaction with a soluble multimeric antigen a solution or a surface assay,
iii) in case of an affinity-driven interaction with a surface bound antigen a solution assay, or
iv) in case of an avidity-driven interaction with a surface bound antigen a surface assay
for determining the binding interaction of the antibody of the human IgG1 subclass with the multimeric antigen.

In one embodiment the binding affinity is determined in solution using an enzyme linked immunosorbent assay (ELISA) or surface plasmon resonance.

In one embodiment the binding affinity is determined using a cellular assay using fluorescence activated cell sorting (FACS) or a cellular effect.

In one embodiment the binding affinities determined in step 1) and 2) of the antibody to the multimeric antigen are comparable if the binding affinities determined in both steps differ by 100% or less (the smaller value is set to 100%) and is different if the binding affinities determined in both steps differ by more than 100% (the smaller value is set to 100%).

In one embodiment the binding affinities determined in step 1) and 2) of the antibody to the multimeric antigen are comparable if the binding affinities determined in both steps differ by a factor of 2 or less (the smaller value is used as basis for the calculation; set to 100%) and is different if the binding affinities determined in both steps differ by more than a factor of 2 (the smaller value is set to 100%).

In one embodiment the binding affinities determined in step 1) and 2) of the antibody to the multimeric antigen are comparable if the ratio of the binding affinities determined in both steps is between 1.5 and 0.5 (the value of step 1) is the denominator and the value of step 2) is the numerator) and is different if the ratio of the binding affinities determined in both steps is less than 0.5.

In one embodiment the binding affinities determined in step 1) and 2) of the antibody to the multimeric antigen are comparable if the binding affinities determined in both steps differ by 75% or less (the smaller value is set to 100%) and is different if the binding affinities determined in both steps differ by more than 75% (the smaller value is set to 100%).

In one embodiment the binding affinity is determined (under in vivo-like conditions) with an antibody:multimeric antigen ratio of 10 or more.

In one embodiment the binding affinity is determined with a molar ratio of multimeric antigen to binding sites of less than 1.

In one embodiment the polypeptide that is derived from lysine-gingipain of *Porphyromonas gingivalis* is the lysine-gingipain of *Porphyromonas gingivalis*. In one embodiment the polypeptide that is derived from lysine-gingipain of *Porphyromonas gingivalis* comprises the amino acid sequence of SEQ ID NO: 02 or SEQ ID NO: 03 or SEQ ID NO: 04 or is a functional variant thereof. In one embodiment the lysine-gingipain of *Porphyromonas gingivalis* has the amino acid sequence of SEQ ID NO: 02 or SEQ ID NO: 03 or SEQ ID NO: 04 or is a functional variant thereof. In one embodiment the polypeptide that is derived from lysine-gingipain of *Porphyromonas gingivalis* has an amino acid sequence that comprises at least residues 230 to 739 of SEQ ID NO: 01.

In one embodiment the incubating is at a pH of (from pH) 7.5 to (pH) 8.5, in the presence of a reducing agent, at a temperature of (from) 30° C. to 42° C., for a time of (from) 10 min. to 240 min. to cleave the antibody into Fabs and Fc-region.

In one embodiment the reducing agent is selected from the group consisting of 2-mercaptoethanol, cysteine, and dithiothreitol. In one embodiment the reducing agent is cysteine. In one embodiment the reducing agent is cysteine at a concentration of from 0.5 mM to 10 mM.

In one embodiment the pH value is about pH 8.

In one embodiment the temperature is (of from) 35° C. to 38° C.

In one embodiment the incubating is for a time of about 60 min.

In one embodiment the antibody comprises in the Fc-region the mutations P329G, L234A and L235A in both heavy chain polypeptides.

In one embodiment of all aspects the incubated mixture is used for the determination of the binding affinity without intermediate purification.

In one embodiment of all aspects the determining of the binding affinity is by surface plasmon resonance.

DETAILED DESCRIPTION OF THE INVENTION

The current invention is in the field of (functional) immunoassays. Especially herein is reported a method for the selection of a (functional) binding assay properly reflecting the binding strength of a therapeutic drug. The therapeutically relevant interaction normally is at a condition in which the target concentration is lower (or at most equal) to the concentration of the therapeutic drug. A digest with the lysine-gingipain of *Porphyromonas gingivalis* under this (concentration) conditions allows the determination of the therapeutically relevant interaction (affinity or avidity) of a therapeutic drug for a given target. This means in the presence of the respective target. This case (use of the monovalent binders) is only required for multimeric (e.g. dimeric) soluble targets, or cell-surface targets.

An affinity-driven interaction mode requires a solution assay, whereas an avidity-driven interaction requires a surface assay for the respective determination. Applying the wrong assay formats would result in wrong assay results.

Functional assays are used for analyzing therapeutic molecules. When functional assays should be indicative for the in vivo binding strength of the drug to the target it needs to be ensured that this in vivo interaction mode (affinity or avidity) is reflected in vitro in the functional assay. This is especially relevant when the drug is bivalent (polyvalent) for a given target. One approach to evaluate the interaction mode is the generation of monovalent drugs by proteolytic digestion and to compare the binding strength before and after the digest in a setting which is representative for the in vivo situation. This however typically requires the purification of the digested monovalent drug, since the protease, the not completely digested drug still being bivalent (polyvalent), and only partially digested drug can compromise assay results.

Taken together, the used protease cleaves the drug highly specifically and quantitatively. Therefore, the binding strength of the drug can be evaluated before and after the digest without purification. A reduction of binding strength upon the digest compared to the non-digested drug indicates an avid binding mode. In cases of not having a difference before and after the digest the binding mode is affine. Keeping the determined binding mode (affine or avid) in a functional assay is crucial for obtaining assay results which are indicative of the in vivo binding strength. Also, keeping the determined binding mode (affine or avid) between assays is necessary for obtaining comparable assay results.

Definitions

Interaction mode can be either affinity or avidity-driven. A measure for the interaction mode is the binding strength.

The terms target and antigen are used interchangeably herein.

The term therapeutic molecule, drug, antibody, and bispecific molecule are used interchangeably herein.

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991) and is referred to as "numbering according to Kabat" herein. Specifically, the Kabat numbering system (see pages 647-660) of Kabat, et al., Sequences of Proteins of Immunological Interest, 5th ed., Public Health Service, National Institutes of Health, Bethesda, Md. (1991) is used for the light chain constant domain CL of kappa and lambda isotype, and the Kabat EU index numbering system (see pages 661-723) is used for the constant heavy chain domains (CH1, Hinge, CH2 and CH3, which is herein further clarified by referring to "numbering according to Kabat EU index" in this case).

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

The term "lysine-gingipain of *Porphyromonas gingivalis*" denotes a polypeptide that specifically cleaves human IgG1 and IgG3 subclass heavy chains between positions 238 and 239 according to the Kabat numbering system (positions 225 and 226 according to EU numbering system), i.e. the hinge region amino acid sequence DKTHTCPPCPA-PELLGGPSVF (SEQ ID NO: 05) is cleaved after the second amino acid residue resulting in the fragments DK (SEQ ID NO: 06) and THTCPPCPAPELLGGPSVF (SEQ ID NO: 07). In one embodiment the polypeptide, i.e. the lysine-gingipain of *Porphyromonas gingivalis*, comprises the amino acid sequence of SEQ ID NO: 02 or SEQ ID NO: 03 or SEQ ID NO: 04 or a functional variant thereof. In one embodiment the polypeptide, i.e. the lysine-gingipain of *Porphyromonas gingivalis*, has an amino acid sequence that comprises at least residues 230 to 739 of SEQ ID NO: 01. The "lysine-gingipain of *Porphyromonas gingivalis*" has the EC number 3.4.22.47 and is also denoted as gingipain K, KGP, Lys-gingipain, PrtP proteinase, lysine-specific cysteine protease, lysine-specific gingipain, lysine-specific gingipain K, or lysine-specific gingipain proteinase. The full length amino acid sequence of an exemplary lysine-gingipain of *Porphyromonas gingivalis* is denoted in SEQ ID NO: 01. This polypeptide is an endopeptidase with strict specificity for lysyl bonds. The enzymatic activity of the polypeptide is activated by the addition of about 30 2-mercaptoethanol, about 50 mM cysteine, about 30 mM dithiothreitol, about 2 mM EDTA, about 2 mM EGTA or glutathione. It is active in the pH range from pH 6.5 to pH 9.5, with a pH of from about pH 7.5 to about pH 8.5 (preferably about pH 8.0) being suitable for the hydrolysis of immunoglobulins. In an exemplary IgG degradation method the following conditions are used: IgG (final concentration 15 μM), KGP (final concentration 10 nM active protease), Tris buffer (0.1 mol/L, pH 8.0), EDTA (final concentration 1 mM), L-cysteine (final concentration 2 mM), 37° C. Human IgGs are cleaved once but if the glycostructures are removed a second cleavage might occur. The enzymatic cleavage can be negatively affected if chaotropic reagents and/or detergents are present. Thus, in one embodiment the method is performed in the absence of chaotropic reagents and/or detergents from all solutions used in the method.

The term "full-length antibody" denotes an antibody which comprises two so called light immunoglobulin chain polypeptides (light chain) and two so called heavy immunoglobulin chain polypeptides (heavy chain). Each of the heavy and light immunoglobulin chain polypeptides of a full-length antibody contains a variable domain (variable region) (generally the amino terminal portion of the polypeptide chain) comprising binding regions that are able to interact with an antigen. Each of the heavy and light immunoglobulin chain polypeptides of full-length antibody comprises a constant region (generally the carboxyl terminal portion). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q). The variable domain of an antibody's light or heavy chain in turn comprises different segments, i.e. four framework regions (FR) and three hypervariable regions (CDR).

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal are highly specific, being directed against a single antigenic site. Furthermore, in contrast to polyclonal antibody preparations, which include different antibodies directed against different antigenic sites (determinants or epitopes), each monoclonal antibody is directed against a single antigenic site on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies and is not to be construed as requiring production of the antibody by any particular method.

The "Fc-region" of an antibody is not involved directly in binding to the antibody's antigen, but exhibits various effector functions. Depending on the amino acid sequence of the constant region of the heavy chains, antibodies (immunoglobulins) are divided in the classes: IgA, IgD, IgE, IgG, and IgM. Some of these classes are further divided into subclasses (isotypes), i.e. IgG in IgG1, IgG2, IgG3, and IgG4, or IgA in IgA1 and IgA2. According to the immunoglobulin class to which an antibody belongs are the heavy chain constant regions of immunoglobulins are called □□□IgA), □(IgD), □(IgE)□□□(IgG), and □ (IgM), respectively. The antibodies according to the invention belong preferably to the IgG class. An "Fc-region of an antibody" is a term well known to the skilled artisan and defined on basis of the papain cleavage of antibodies.

Functional Assays:

The current invention is in the field of immunoassays. Especially herein is reported a method for the selection of an in-vivo like assay for multispecific binder, such as e.g. a bispecific antibody.

A multispecific binder is a molecule that binds to multiple different interaction partners, whereby each target/interaction partner can be bound mono- or multivalently. For example, a bispecific binder specifically binds to two different targets/interaction partners, whereby each target/interaction partner can be bound mono- or bivalently. For example, antibodies, such as full length antibodies of the IgG class, are bivalent. Thus, when determining the affinity it should be a "true" affinity avoiding the avidity effect of the bivalent binder. To determine the affinity and binding kinetics of antibodies binding bi- or multivalent targets it is therefore necessary to turn the bivalent antibodies into monovalent binding entities like fragment antigen-binding (Fab) units. Currently methods for the determination of the affinity of bivalent antibodies are two step methods:

1: cleavage of the antibody to be analyzed to generate monovalent binding entities, and
2: purification of the reaction mixture of 1.

Alternatively it is possible to re-clone and express the Fab fragment for which even more time and labor are required as for the approach outlined above.

In order to determine the interaction strength of a multispecific binder with each of its targets/interaction partners individual assays for determining the specificity and affinity to each of the targets/interaction partners have to be selected and performed in order to fully characterize all interactions of the multispecific binder.

In the following the concept is outlined with a bispecific antibody. This is done merely as an exemplification and shall not be construed to limit the scope of the current invention which is set forth in the appended claims.

A bispecific antibody is a binder that comprises at least one binding site for a first antigen and at least one binding site for a second antigen.

A bispecific antibody can comprise one binding site for a first antigen and one binding site for a second antigen. In this case the bispecific antibody is monovalent for each of its antigens and in total bivalent. Thus, the simplest form of a multispecific binder is a bivalent bispecific antibody. This format is also denoted as a 1+1 format.

A bispecific antibody can also comprises two binding sites for a first antigen and one binding site for a second antigen. Such a bispecific antibody is a trivalent bispecific antibody. This format is also denoted as a 2+1 format.

A bispecific antibody can also comprises two binding sites for a first antigen and two binding sites for a second antigen. Such a bispecific antibody is a tetravalent bispecific antibody. This format is also denoted as a 2+2 format.

Further the bispecific antibody can be a full-length antibody. The term "full-length antibody" denotes an immunoglobulin which comprises two so called antibody light chain polypeptides (short: light chain) and two so called antibody heavy chain polypeptides (short: heavy chain). Each of the antibody heavy and light chain polypeptides of a full-length antibody comprises a variable domain (variable region) (generally the amino terminal portion of the polypeptide chain). Each of the antibody heavy and light chain polypeptides of a full-length antibody comprises a constant region (generally the carboxyl terminal portion). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q). The variable domain of an antibody's light or heavy chain in turn comprises different segments, i.e. four framework regions (FR) and three hypervariable regions (CDR), and interacts with an antigen via its hypervariable regions in the variable domains. The pair of an antibody heavy chain variable domain and the cognate antibody light chain variable domain is denoted as binding site.

The term "solution assay" denotes an assay wherein the therapeutic drug, e.g. the antibody, is immobilized on a solid phase and the target is applied in soluble form (i.e. as soluble target). A solution assay can also be an intracellular assay in which the target is present in the cytoplasm of the cell.

The term "surface assay" denotes an assay wherein the target is on a solid phase and the therapeutic drug, e.g. the antibody, is applied in soluble form. The solid phase can be any solid phase conventionally used in immunoassays or the surface of a cell expressing the target.

The decision tree underlying the current invention is shown in FIG. 1.

If the bispecific antibody is monovalent for the respective antigen (target/interaction partner) then either a solution assay or a solid-surface-based assay can be used.

If the bispecific antibody is bivalent for its antigen (target/interaction partner) then it depends on the kind of the antigen (target/interaction partner), i.e. soluble or surface-bound, which assay format should be chosen:
  in case of a monomeric soluble antigen (target/interaction partner) only a solution assay can be used;
  in case of an affinity-driven interaction with a soluble multimeric antigen (target/interaction partner) only a solution assay can be used;
  in case of an avidity-driven interaction with a soluble multimeric antigen (target/interaction partner) either a solution or a solid-surface-based assay can be used;
  in case of an affinity-driven interaction with a surface bound antigen (target/interaction partner) only a solution assay can be used;
  in case of an avidity-driven interaction with a surface bound antigen (target/interaction partner) only a solid-surface-based assay can be used;

Thus, in order to make this decision the interaction of the bispecific antibody with the antigen (target/interaction partner), for which the bispecific antibody is bivalent, has to be classified as affinity-driven or avidity-driven.

The term "affinity-driven interaction" denotes an interaction between a binder and its target/interaction partner whose strength is not dependent on the number of interaction sites in the binder for the target/interaction partner in question. Thus, affinity describes the strength of a single interaction between antibody and its antigen. A bivalent antibody of the IgG class has two antigen-binding sites, and the avidity is commonly applied to antibody interactions in which multiple antigen-binding sites simultaneously interact with the target antigen, often in multimeric structures.

The term "avidity-driven interaction" denotes an interaction between a binder and its target/interaction partner whose strength is dependent on the number of interaction sites in the binder for the target/interaction partner in question. Thus, avidity of an antibody refers to the accumulated strength of multiple affinities. Avidity is commonly obtained regarding interactions in which multiple antigen-binding sites, often in multimeric structures, are involved. To determine the affinity of antibodies it is necessary to convert the bivalent antibodies into monovalent binding entities like antigen-binding fragments (Fab).

An affinity-driven interaction of a bispecific antibody can be distinguished from an avidity-driven interaction by analyzing the dependency of the interaction strength of the bispecific antibody with the antigen (target/interaction partner) in question on the number of binding sites in the antibody for the antigen (target/interaction partner) in question.

In case the interaction strength does not depend on the number of binding sites then the interaction is affinity-driven. But if the interaction strength does depend on the number of binding sites then the interaction is avidity driven.

Thus, the interaction strength has to be determined twice: once for the bispecific antibody and once for the bispecific antibody or a fragment thereof that is only monovalent for the antigen (target/interaction partner) in question.

Different antibody fragments are described in the following:
  the F(ab')2 fragment:
  the F(ab')2 fragment has a molecular weight of about 110 kDa and comprises the two antigen-binding site of a full length antibody of the IgG class connected via the hinge-region disulfide bonds; it is void of most, but not all, of the Fc-region
  Fab' fragment:
  the Fab' fragment has a molecular weight of about 55 kDa; it can be formed by the reduction of the hinge-region disulfide bonds of a F(ab')2 fragment; the Fab' fragment comprises a free sulfhydryl group; as it is derived from F(ab')2 it may contain a small portion of the Fc.-region
  fragment antigen binding—Fab:
  the Fab has a molecular weight of about 50 kDa; it is a monovalent binding fragment that can be obtained from antibodies of the IgG and IgM class; it comprises the VH and CH1 domains of the heavy chain and a complete light chain both linked by an intramolecular disulfide bond
  Fv fragment:
  the Fv fragment has a molecular weight of about 25 kDa; it is the smallest antibody fragment that contains a complete antigen-binding site (VH domain and VL domain); the VH and VL domains of the Fv fragment are held together by non-covalent interactions
  "rIgG" fragment:
  the "rIgG" fragment denotes a half-antibody that is obtained by reducing just the hinge-region disulfide bonds of a full length antibody (e.g. using 2-MEA); it has a molecular weight of about 75 kDa
  fragment crystallizable—Fc-fragment:
  the Fc-fragment has a molecular weight of about 50 kDa; it comprises the CH2 and CH3 domains of the heavy chain of a full length antibody and part of the hinge region; the two chains are held together by one or more disulfide bonds (in the hinge region); the Fc-fragment cannot bind the antigen, but it is responsible for the effector functions of the full length antibody.

Especially preferred and commonly used is the Fab.

A monovalent fragment can be obtained e.g. by re-cloning and expression of the respective Fab fragment. This is a time and labor-intensive approach.

Alternatively it is possible to cleavage of the antibody to be analyzed to generate monovalent binding entities. This can be done enzymatically.

Often, Fab fragments are generated by partial proteolytic digestions of IgGs with unspecific proteases like papain or pepsin, which cleave above or below the hinge region, respectively. The fragments contain the disulphide bonds that join the heavy chains, but the cleavage is below the site of the disulphide bond between the light chain and heavy chain (Porter, 1959; Nisonoff et al., 1960; Akita and Nakai, 1993, Andrew and Titus, 2003; Mage, 1987; Zhao et al., 2009; Andrew, S. M. and J. A. Titus. 2003).

IgGs digested with pepsin results in F(ab')2 fragments that are subsequently mildly reduced to give Fab' fragments. Most likely the hinge region is more susceptible to the attack of proteases as it is exposed and flexible. Subsequently, the fragments are then purified from the digestion mix.

However, lack of reproducibility, uncut IgG and overdigestion is often a problem.

With papain digestion, e.g., it is difficult to obtain homogeneous Fabs (Parham, 1983; 1986; Mage, 1987). Immobilized papain products (e.g. papain agarose resins; see e.g. Tischer, W., and V. Kasche, 1999; Luo, Q., et al. 2002) allow better control of the digestion reaction and efficient removal of the Fab and Fc fragments from the crude protease digest; nevertheless purification is still required.

Another approach to obtain monomeric antigen-binding fragments include the generation of F(ab')2 fragments by digestion with Immunoglobulin G-degrading enzyme of *S. pyogenes* (IdeS) and mild reduction with 2-mercaptoethylamine (2-MEA) to generate Fab' fragments (von Pawel-Rammingen, U., et al. 2002+2003; Ishikawa, E. and S. Yoshitake, 1980; DeSilva, B. S., et al., 1995).

The two antigen-binding domains of an antibody of the IgG class can also be obtained by reducing the IgG to two half-IgGs (rIgG; see e.g. Billah, M. M., et al., 2010). It is the product of selectively reducing just the hinge-region disulphide bonds which are the most accessible and easiest to reduce, especially with a mild reducing agents like 2-MEA.

Finally, a Fab can also be obtained by recombinant expression of the light chain and the heavy chain Fd-fragment (VH-CH1) (Zhao et al., 2009). This is however time consuming and laborious if several different Fabs are needed for e.g. a comparison.

A limited digestion using the endoproteinase Lys-C in a 40 min digestion of hIgG1's to analyze the chain assembly by mass spectrometry has been reported in PCT/EP2015/057164. Using this procedure Lys-C exclusively cuts once above the hinge region generating Fab and Fc-fragments.

A protease that cleaves selectively in the upper hinge region of antibodies of the IgGs class is streptococcal erythrogenic toxin B (SpeB) from *S. pyogenes* (von Pawel-Rammingen, U., et al. 2002). This protease requires reducing agent like DTT or TCEP in the range of 1-5 mM for activity (Persson, H., et al., 2013) resulting in the concomitant reduction of the interchain thiols of the digested antibody.

IgG-specific proteases and their cleavage sites are shown in the following Table (see also Brerski, R. J. and Jordan, R. E., mAbs 2 (2010) 212-220).

| protease | specificity | recognition sequence | fragments |
|---|---|---|---|
| palsmin | | DK↓THTCPPCPAPELLGGPSVF (SEQ ID NO: 05) | 2xFab 1xFc |
| lysine-gingipain of porphyromonas gingivalis | human IgG1 and IgG3, IgA | DK↓THTCPPCPAPELLGGPSVF | 2xFab 1xFc |
| human neutrophil elastase | | DKT↓HTCPPCPAPELLGGPSVF | 2xFab 1xFc |
| papain | IgG, specific only in limited proteolysis | DKTH↓TCPPCPAPELLGGPSVF | 2xFab 1xFc |
| streptococcal erythrogenic toxin B (SpeB) from *S. pyogenes* | | DKTHT↓CPPCPAPELLGGPSVF | 2xFd 2xLC 1xFc |
| glutamyl endopeptidase I from *S. aureus*, Cathepsin G | | DKTHTCPPCPAPE↓LLGGPSVF | 1xF(ab')2 |
| pepsin | IgG1 > IgG2 | DKTHTCPPCPAPEL↓LGGPSVF | 1xF(ab')2 multiple HC-Fc fragments |
| Immunoglobulin G-degrading enzyme of *S. pyogenes* (IdeS) | | DKTHTCPPCPAPELLG↓GPSVF | 1xF(ab')2 |

The *P. gingivalis* proteases have been studied since more than 30 years. They have been identified as cysteine-proteinases requiring the presence of reducing agents for activity. One of them is the cysteine protease gingipain K (EC. 3.4.22.47).

Scott et al. purified lysine-gingipain of *Porphyromonas gingivalis* (KGP) back in 1993 (Scott, C. F., et al., J. Biol. Chem. 268 (1993) 7935-7942).

Scott et al. identified cysteine, dithiothreitol, glutathione and 2-mercaptoethanol to be suitable reducing agents for the activation of KGP.

KGP cleaves peptides with Lys in the P1 position, and the residue at P2 appears to be less important. However, if P2 is occupied by Lys or Arg, hydrolysis appears to be blocked. KGP is capable of hydrolyzing protein substrates such as BSA, casein, hemoglobin, acid-soluble human placental type I collagen, human IgG, and IgA (Curtis, M. A., et al., Crit. Rev. Oral Biol. Med. 12 (2001) 192-216).

The amino acid sequence of lysine-gingipain of *Porphyromonas gingivalis* including an identification of the respective domains was reported by Okamoto, K., et al. (J. Biochem. 120 (1996) 398-406). The kgp gene was reported and deposited by Slakeski, N., et al. under accession number U75366 and AAB60809.1 (Oral Microbiol. Immunol. 14 (1999) 92-97). Several C-terminally truncated but active forms have been identified. It has been found that for the C-terminally truncated proteins KGP($\Delta$1292-1732), KGP ($\Delta$1157-1732), KGP($\Delta$738-1732), KGP($\Delta$681-1732) and KGP($\Delta$602-1732) enzymatic activity was only barely measurable for the last two mutants (see e.g. Sztukowska, M., et al., Mol. Microbiol. 54 (2004) 1393-1408).

KGP has a narrow specificity for synthetic substrates, limited to peptide bonds containing arginine and lysine residues, respectively, but they can nevertheless degrade immunoglobulins G and A in a limited degradation manner (Yamamoto, K., et al., In: Proteases: new Perspectives (1999), V. Turk (ed.), Birkhauser Verlag Basel (CH), 175-184; Yamamoto, K., et al., In: N Katunuma, H Kido, H Fritz, J Travis (Eds): Medical Aspects of Proteases and Protease Inhibitors. IOS Press, Amsterdam, 139-149; Kadowaki, T., et al., J. Biol. Chem. 269 (1994) 21371-21378; Abe, N., et al., J. Biochem. 123 (1998) 305-312).

Comparative properties of envelope-associated arginine-gingipains (RGP) and lysine-gingipain (KGP) of *Porphyromonas gingivalis* have been reported in 1998 by Fujimura et al. (Microbiol. Lett. 163 (1998) 173-179). The enzymes were commonly activated by reducing reagents such as mercaptoethanol, dithiothreitol and cysteine. RGP-B was activated markedly by glycyl-glycine and KGP was activated significantly by EDTA and EGTA. The hydrolytic activities of RGPs and KGP to chromogenic synthetic substrates were limited to the compounds with arginine and lysine in the P-1 positions, respectively. When IgG was treated with the three enzymes separately, it was demonstrated that two new fragments of 34 kDa and 15 kDa (SDS under reducing conditions) were generated in each reaction product. The optimum pH for the activity of KGP was found to be 7.5. Thiol reagents activated both RGPs and KGP, whereas dithiothreitol was the best activator of KGP (at 20-30 mM), followed by mercaptoethanol (at 20-30 mM) and cysteine (at more than 1.5 mM but less than 10 mM). KGP split only X-Y-Lys-pNA.

Vincents, B., et al. reported that gingipain K of *Porphyromonas gingivalis* can hydrolyze subclass 1 and 3 of human IgG, whereby the heavy chain of IgG1 was cleaved at a single site within the hinge region, generating Fab and Fc fragments and that IgG3 was also cleaved within the heavy chain, but at several sites around the CH2 region (FASEB J., 25 (2011) 3741-3750). Cleavage of IgG2 is not mediated by KGP (Guentsch, A., et al., J. Periodont. res. 48 (2013) 458-465).

An high-resolution crystal structure of KGP active site was reported by de Diego, I., et al. suggesting that catalysis may require a catalytic triad, Cys477-His444-Asp388, rather than the cysteine-histidine dyad normally found in cysteine peptidases (J. Biol. Chem. 289 (2014) 32291-32302).

The Method as Reported Herein

Herein is reported a fast and easy method for the selection of a (functional) immunoassay for a multispecific binder that has one or more binding site for a multimeric target/interaction partner.

The method is based on the comparison of the binding strength between the full-length multispecific binder and a fragment thereof that is monovalent for the target/interaction partner.

The required monovalent fragments can be e.g. Fabs. Fabs are obtained from the full-length antibodies of the IgG1 subclass by enzymatic digestion. It has been found that the lysine-gingipain of *Porphyromonas gingivalis* can be used for the generation of Fabs from full length antibodies comprising a hinge region of an antibody of the human IgG1 subclass. With this enzyme a highly specific and quantitative protease digestion generating a homogenous pool of intact Fab and Fc-fragments without any over-digestion typically associated with other proteolytic enzymes can be achieved. Additionally the reaction mixture can directly, i.e. without any intermediate purification, be applied to a surface plasmon resonance chip.

In more detail this is done by in solution digestion and direct kinetic affinity determination of the Fab fragment by SPR without any prior purification or cleaning step. The complete digestion by the lysine-gingipain of *Porphyromonas gingivalis* of human IgG1s was verified by ESI-QTOF-MS.

This digestion method can be used for the determination of kinetic rate constants of human or humanized antibodies, e.g. of the subclass IgG1 or comprising an Fc-region derived from the human subclass IgG1, specifically binding to di- or multimeric antigens using a surface plasmon resonance method. The method comprises in one embodiment the following steps: 1) incubating the antibody with the lysine-gingipain of *Porphyromonas gingivalis* to cleave it completely generating a homogenous pool of Fabs and Fc-fragments, and 2) determining the binding affinity of the Fab in the digestion mixture by surface plasmon resonance (SPR). Direct SPR on the digestion mixture allows precise kinetic characterization of the Fab fragment without any prior purification.

It has been found that the affinity constants determined by SPR of Fabs of antibodies of the IgG1 subclass obtained by digesting with the lysine-gingipain of *Porphyromonas gingivalis* without subsequent purification correspond to affinity constants of Fabs obtained by recombinant expression, or by digesting with papain and subsequent purification prior to SPR measurement.

One aspect as reported herein is a method for determining the binding interaction of an antibody of the human IgG1 subclass with a multimeric antigen, whereby the antibody has at least two binding sites specifically binding to the antigen, comprising the following steps:

1) determining the binding affinity of the antibody for the multimeric antigen,
2) incubating a mixture comprising the antibody, the antigen and a polypeptide that is derived from lysine-gingipain of *Porphyromonas gingivalis* under conditions and for a time sufficient to cleave the antibody into Fabs and Fc-region, whereby the concentration of the antibody is higher than the concentration of the antigen, and determining the binding affinity of the Fabs of the antibody for the multimeric antigen, and determining the binding affinity of the antibody to the multimeric antigen to be affinity-driven if the binding affinity determined in both steps is comparable and to be avidity-driven if the binding affinity determined in both steps is different.

One aspect as reported herein is a method for selecting the assay format for determining the binding interaction of an antibody of the human IgG1 subclass with a multimeric antigen, whereby the antibody has at least two binding sites specifically binding to the antigen, comprising the following steps:

1) determining the binding affinity of the antibody for the multimeric antigen,
2) incubating a mixture comprising the antibody, the antigen and a polypeptide that is derived from lysine-gingipain of *Porphyromonas gingivalis* under conditions and for a time sufficient to cleave the antibody into Fabs and Fc-region, whereby the concentration of the antibody is higher than the concentration of the antigen, and determining the binding affinity of the Fabs of the antibody for the multimeric antigen, whereby the binding affinity of the antibody to the multimeric antigen is i) affinity-driven if the binding affinity determined in both steps is comparable, or ii) avidity-driven if the binding affinity determined in both steps is different, and selecting
  i) in case of an affinity-driven interaction with a soluble multimeric antigen a solution assay,
  ii) in case of an avidity-driven interaction with a soluble multimeric antigen a solution or a surface assay,
  iii) in case of an affinity-driven interaction with a surface bound antigen a solution assay, or
  iv) in case of an avidity-driven interaction with a surface bound antigen a surface assay for determining the binding interaction of the antibody of the human IgG1 subclass with the multimeric antigen.

In one embodiment the binding affinity is determined using an ELISA.

In one embodiment the binding affinity is determined using a surface plasmon resonance method.

In one embodiment the same assay is used in step 1) and step 2).

In one embodiment the binding affinity is determined using FACS or a cellular effect.

The term "specifically binding (to an antigen)" denotes the binding of an antibody to its antigen in an in vitro assay, in one embodiment in a binding assay in which the antibody is bound to a surface and binding of the antigen to the antibody is measured by surface plasmon resonance (SPR). Specifically binding means a binding affinity ($K_D$) of $10^{-8}$ M or less. An exemplary SPR method is a BIAcore assay (GE Healthcare Biosensor AB, Uppsala, Sweden). The affinity of the binding is defined by the terms $k_a$ (rate constant for the association of the antibody from the antibody/antigen complex), $k_d$ (dissociation constant), and $K_D$ ($k_d/k_a$). At the same time the property of not binding to an antigen is ensured by a $K_D$ of $10^{-7}$ mol/L or worse, e.g. of $10^{-5}$ mol/L. In one embodiment the antibody $K_D$-gap of at least 100-fold between specifically binding to an antigen and not specifically binding to an antigen, respectively.

In one embodiment the incubated reaction mixture of step 2) is directly applied in the surface plasmon resonance method.

In one embodiment the binding affinities determined in step 1) and 2) of the antibody to the multimeric antigen is comparable if the binding affinities determined in both steps differ by 100% or less (the smaller value is set to 100%) and is different if the binding affinities determined in both steps differ by more than 100% (the smaller value is set to 100%).

In one embodiment the method comprises the following steps:

1) determining the binding affinity of the antibody for the multimeric antigen using a surface plasmon resonance method,
2) incubating a mixture comprising the antibody, the antigen and a polypeptide that is derived from lysine-gingipain of *Porphyromonas gingivalis* at a pH of from pH 7.5 to pH 8.5, in the presence of a reducing agent, at a temperature of from 30° C. to 42° C., for time of from 10 min. to 240 min. to cleave the antibody into Fabs and Fc-region, whereby the concentration of the antibody is higher than the concentration of the antigen, and determining the binding affinity of the Fabs of the antibody for their antigen using a surface plasmon resonance method by directly applying the incubated reaction mixture obtained in the previous step in the surface plasmon resonance method.

In one embodiment the method for selecting the assay format for determining the binding interaction of an antibody of the human IgG1 subclass with a multimeric antigen, whereby the antibody has at least two binding sites specifically binding to the antigen, comprises the following steps:

1) determining the binding affinity of the antibody for the multimeric antigen using a surface plasmon resonance method,
2) incubating a mixture comprising the antibody, the antigen and a polypeptide that is derived from lysine-gingipain of *Porphyromonas gingivalis* at a pH of from pH 7.5 to pH 8.5, in the presence of a reducing agent, at a temperature of from 30° C. to 42° C., for time of from 10 min. to 240 min. to cleave the antibody into Fabs and Fc-region, whereby the concentration of the antibody is higher than the concentration of the antigen, and determining the binding affinity of the Fabs of the antibody for their antigen using a surface plasmon resonance method by directly applying the incubated reaction mixture obtained in the previous step in the surface plasmon resonance method, whereby the binding affinity of the antibody to the multimeric antigen is i) affinity-driven if the binding affinity determined in both steps is comparable, or ii) avidity-driven if the binding affinity determined in both steps is different, and selecting
  i) in case of a monomeric soluble antigen a solution assay,
  ii) in case of an affinity-driven interaction with a soluble multimeric antigen a solution assay,
  iii) in case of an avidity-driven interaction with a soluble multimeric antigen a solution or a surface assay, iv) in case of an affinity-driven interaction with a surface bound antigen a solution assay, or v) in case of an avidity-driven interaction with a surface bound antigen a surface assay for determining the binding interaction of the antibody of the human IgG1 subclass with the multimeric antigen.

In one embodiment the incubating is under in vivo conditions. In one embodiment the incubating is with an antibody: multimeric antigen ratio of 10 or more. In one embodiment in the incubating the concentration of the antibody is at least 10 times the concentration of the antigen.

In one embodiment the polypeptide that is derived from lysine-gingipain of *Porphyromonas gingivalis* is the lysine-gingipain of *Porphyromonas gingivalis*. In one embodiment the polypeptide that is derived from lysine-gingipain of *Porphyromonas gingivalis* comprises the amino acid sequence of SEQ ID NO: 02 or SEQ ID NO: 03 or SEQ ID NO: 04 or a functional variant thereof. In one embodiment the polypeptide that is derived from lysine-gingipain of *Porphyromonas gingivalis* has an amino acid sequence that comprises at least residues 230 to 739 of SEQ ID NO: 01.

In one embodiment the reducing agent is selected from the group consisting of 2-mercaptoethanol, cysteine, and dithiothreitol. In one embodiment the reducing agent is cysteine. In one embodiment the reducing agent is cysteine at a concentration of from 0.5 mM to 10 mM. In one embodiment the reducing agent is cysteine at a concentration of about 2 mM.

In one embodiment the pH value is about pH 8.

In one embodiment the temperature is of from 35° C. to 38° C. In one embodiment the temperature is about 37° C.

In one embodiment the incubating is for a time of from 30 min. to 120 min. In one embodiment the incubating is for a time of about 60 min.

In one embodiment the antibody comprises in the Fc-region the mutations P329G, L234A and L235A in both heavy chain polypeptides.

In one embodiment the antigen is multimeric antigen. In one embodiment the antigen is a homo-multimeric antigen. In one embodiment the antigen is selected from the group consisting of vascular endothelial growth factor A (VEGF-A), carcinoembryonic antigen (CEA), angiopoietin-2 (ANG2), and fibroblast activation protein (FAP).

The method as reported herein allows for a fast determination of the binding affinity of a bivalent antibody for its multimeric antigen without the requirements to recombinantly produce a single binding site version of the antibody. With the method as reported herein the determination of the biding affinity of the bivalent antibody for its antigen is possible without the need for an intermediate purification of the reaction mixture that has been used for the generation of the Fabs of the bivalent antibody.

The method as reported herein has been exemplified in the following with the antibody bevacizumab. Bevacizumab is a humanized anti-VEGF antibody of the human IgG1 subclass. The therapeutic antibody bevacizumab binds a dimeric antigen, i.e. VEGF-A.

The quality of the bevacizumab Fabs and digests was analyzed by UHR ESI-QTOF mass spectrometry. The deconvoluted mass spectra of the purified Fab following a papain digest, and a purified recombinant Fab provided proof for the high quality of both materials as only the masses of the Fab fragments could be detected.

In more detail, complete digestion of bevacizumab by the lysine-gingipain of *Porphyromonas gingivalis* was verified by electrospray ionization mass spectrometry after desalting of the reaction mixture using a size exclusion chromatography. No fragmentation or side products could be identified in the MS spectra.

For comparison bevacizumab has been digested using the enzyme papain. Form the MS spectra it can be seen that papain is not suitable for functional assessment due to unspecific fragmentation of the antibody and loss of function.

The respective MS-spectra are shown in FIG. 2 (one hour digestion with the lysine-gingipain of *Porphyromonas gingivalis*), FIG. 3 (1.5 hours digestion with papain), and FIG. 4 (2 hour digestion with papain). It can be seen that no antibody fragmentation beside the single cleavage in the hinge region occurred when the lysine-gingipain of *Porphyromonas gingivalis* was used.

In more detail, the quality of the recombinant bevacizumab Fab and papain and lysine-gingipain of *Porphyromonas gingivalis* digests were analyzed by UHR ESI-QTOF mass spectrometry. The deconvoluted mass spectra of the purified Fab following a papain digest, and a purified recombinant Fab revealed the high quality of both materials as only the masses of the intact Fab 48208 Da (theoretical average mass: 48208 Da) and 47726 Da (theoretical average mass: 47726), respectively, could be detected. The evaluation of the mass spectrum of bevacizumab digested with papain revealed not only the presence of the 48207 Da Fab (theoretical average mass: 48208 Da) and the Fc-fragments (multiple masses present due to heterogeneity of the Fc N-glycan's). In addition, unassignable fragments corresponding to the masses x:23422 Da and 23453 Da, y:34587 Da, and z:47607 Da were detected in the papain digest. In contrast the deconvoluted mass spectrum of bevacizumab digested with the lysine-gingipain of *Porphyromonas gingivalis* demonstrated only the presence of the 47969 Da Fab (theoretical average mass: 47970 Da) and the Fc-fragment (multiple masses present due to the Fc N-glycan's). The digestion with the lysine-gingipain of *Porphyromonas gingivalis* was complete without any undigested or single cut IgG (IgG without one Fab) detectable by mass spectrometry. Nor could any unspecific digestion, over-digestion, or further degradation of the fragments be detected in the crude digestion mixture of the lysine-gingipain of *Porphyromonas gingivalis* digest.

The method as reported herein was performed with different bevacizumab-derived samples:

1) full length bivalent antibody
2) recombinantly produced Fab
3) Fab produced with a method as reported herein (without intermediate purification) (determined directly after the incubation and after 24 hours additional incubation in the presence of functional lysine-gingipain of *Porphyromonas gingivalis*)
4) Fab produced with papain (without termination of the reaction and without intermediate purification)
5) Fab produced with papain (with termination of the reaction, without intermediate purification)
6) Fab produced with papain (with intermediate purification)

In order to compare the affinities of the different produced Fabs of bevacizumab the binding affinities of bevacizumab digested with the lysine-gingipain of *Porphyromonas gingivalis* without purification of the Fab and the binding affinities of a recombinant transiently expressed bevacizumab Fab, a purified Fab following a papain digest were determined.

For determining the affinities a murine anti-His-tag antibody was immobilized and the dimeric VEGF-A conjugated to a His-tag was captured on the sensor chip surface. Afterwards, the analytes binding to VEGF-A were injected and flew over the surface. The derived sensorgrams were fitted to a 1:1 Langmuir binding model and used to determine the association rate constants ka, the dissociation rate constants kd, and the binding constants KD. Generally, the rate and binding constants for the Fab fragments were all very similar (see Table below). The binding constant of the Fab in the lysine-gingipain of *Porphyromonas gingivalis* digestion mixture was found to be 1.1 nM, and those of the recombinant Fab and the purified Fab after digestion with papain were determined to 0.8 and 1.0 nM, respectively. The KD of the full length bivalent antibody was determined to be 0.18 nM demonstrating the avid binding to the dimeric VEGF-A. But when the papain digestion mixture was applied to the immobilized chip surface, we did not observe binding to the captured dimeric VEGF-A. Consequently, no binding constant could be determined for the papain digestion mixture. It has been found that the VEGF-A surface was damaged after applying the papain containing samples as it could not be used anymore.

The results are presented in the following Table.

| sample | ka [1/Ms] | kd [1/s] | KD [nM] |
|---|---|---|---|
| full length bevacizumab (avidity) | 1.61E+05 | 2.96E−05 | 0.18 |
| recombinant bevacizumab Fab (affinity) | 9.03E+04 | 7.37E−05 | 0.8 |
| bevacizumab digested lysine-gingipain of porphyromonas gingivalis, without purification (without additional incubation) | 5.18E+04 | 5.83E−05 | 1.1 |
| bevacizumab digested with papain (without termination of the reaction and without intermediate purification) | could not be determined as no binding signal was observed | | |
| bevacizumab digested with papain (with termination of the reaction, without intermediate purification) | could not be determined as no binding signal was observed | | |
| bevacizumab digested with papain (with intermediate purification) | 7.95E+04 | 8.02E−05 | 1.0 |

It can be seen that the binding of bevacizumab to its antigen is avidity-driven as the determined binding affinity is not comparable between the full length bivalent antibody and the monovalent Fab (difference of more than 100%).

It can be seen that as the lysine-gingipain of *Porphyromonas gingivalis* is specific for human IgG1, it does not destroy the immobilized chip surface. In contrast thereto no binding was observed after the not purified papain digestion reaction mixture was applied to the immobilized chip surface. The VEGF surface could not be used any more after applying the papain containing sample as it has been damaged by the presence of papain.

The respective SPR diagrams are shown in FIG. 5A to 5D.

Storage of the lysine-gingipain of *Porphyromonas gingivalis*-digested bevacizumab and repeated affinity determinations by SPR allowed to conclude the digests to be stable at 4° C. for at least 24 and 48 hours, respectively, i.e. no further digestion or fragmentation occurred.

Beside the use of lysine-gingipain of *Porphyromonas gingivalis* for the determination of affinities of human IgG1 s binding di- or multimeric antigens, the protease can also be used in cases where IgG1s binding monomeric antigens are difficult to immobilize on the SPR metal surface.

In addition, the lysine-gingipain of *Porphyromonas gingivalis* will be very beneficial for the structural analysis of the Fab fragments and structure-function relationships of human IgG1-antigen binding at atomic resolution, e.g., by X-ray crystallography. Compared with IgGs, Fab fragments are more amenable to crystallization.

The participation of a second drug binding site in target binding for the in vivo interaction mode was analyzed by comparing intact bivalent monoclonal antibody and said lysine-gingipain of *Porphyromonas gingivalis*-digested antibody binding a soluble oligomeric target in a cell-based assay. As VEGF-A is a soluble dimer, the influence of digestion with lysine-gingipain of *Porphyromonas gingivalis* was evaluated in a VEGF-A-specific cell-based reporter gene assay. In this assay binding of VEGF-A to the VEGF receptor 2 and signal transduction is measured. The bivalent anti-VEGF-A antibody, the antibody digested with lysine-gingipain of *Porphyromonas gingivalis*, a purified Fab fragment of said antibody obtained by papain digestion, and a VEGF-A-monovalent CrossMab were tested and compared. The dose-response curves were comparable for all compounds with $EC_{50}$ values of 1.2, 10.3, 10.4, and 12.1 nM for the intact antibody, the lysine-gingipain of *Porphyromonas gingivalis*-digested antibody, the purified Fab (following papain digestion), and the CrossMab, respectively. The $EC_{50}$ of the bivalent antibody is about 9-10-fold lower than that of the Fab fragment and the monovalent CrossMab. Thus, the two bindings sites of the bivalent anti-VEGF-A antibody increase the binding strength (avidity) to the soluble dimeric VEGF-A. The CrossMab with one binding site towards VEGF-A has similar $EC_{50}$ as the Fab fragments (12.1 versus 10.3-10.4 nM). The lysine-gingipain of *Porphyromonas gingivalis* alone shows no inhibition of VEGF-A (see FIG. 6).

The participation of a second drug binding site in target binding for the in vivo interaction mode was analyzed by comparing intact and lysine-gingipain of *Porphyromonas gingivalis*-digested monoclonal antibody binding a cell-surface-associated target in a cell-based assay. Many therapeutic targets like carcinoembryonic antigen (CEA) are localized to the cell-surface. To evaluate the lysine-gingipain of *Porphyromonas gingivalis*-digest involving an antibody specifically binding to a cell-surface-associated target, an anti-CEA bivalent monoclonal antibody, said antibody digested with lysine-gingipain of *Porphyromonas gingivalis*, and a purified Fab fragment obtained by papain digestion of said bivalent antibody were analyzed in a flow cytometry assay measuring binding to CEA-expressing gastric adenocarcinoma cells via an Alexa Fluor 647-labeled anti-human kappa light chain detection antibody. The integrity of the lysine-gingipain of *Porphyromonas gingivalis*-digested antibody and the purified Fab was confirmed by UHR-ESI-QTOF-MS. The sigmoidal dose-response curve obtained with the bivalent antibody and the linear responses for the lysine-gingipain of *Porphyromonas gingivalis*-digested antibody as well as the purified Fab demonstrate that both binding sites of the antibody are involved in the binding of the cell-surface-target with high binding strength (avidity). No binding could be detected for the negative controls with an antibody binding to a non-related target, nor with the lysine-gingipain of *Porphyromonas gingivalis* alone.

Recombinant Methods:

Antibodies may be produced using recombinant methods and compositions, e.g., as described in U.S. Pat. No. 4,816,567. In one embodiment, isolated nucleic acid encoding an antibody as described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of producing an antibody as reported herein is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR− CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

General chromatographic methods are known to a person skilled in the art e.g. Chromatography, 5th edition, Part A: Fundamentals and Techniques, Heftmann, E. (ed.); Elsevier Science Publishing Company, New York, (1992); Advanced Chromatographic and Electromigration Methods in Biosciences, Deyl, Z. (ed.), Elsevier Science BV, Amsterdam, The Netherlands, (1998); Chromatography Today, Poole, D. F., and Poole, S. K., Elsevier Science Publishing Company, New York, (1991); Scopes, Protein Purification: Principles and Practice (1982); Sambrook, J., et al. (ed.), Molecular Cloning: A Laboratory Manual, Second Edition, Cold Spring Harbor Laboratory Press, Cold Spring Harbor, N.Y., 1989; or Current Protocols in Molecular Biology, Ausubel, F. M., et al. (eds.), John Wiley & Sons, Inc., New York.

SCIENTIFIC CITATIONS USED IN THE PASSAGES ABOVE EXCLUDING PATENTS

Andrew S. M., Titus J. A., 2003, Curr Protoc Cell Biol. Unit 16.4. (Chapter 16).
Mage, E. L. M., 1987, p. 79-97. In: L. B. Schook (Ed.), Monoclonal antibody production techniques and applications, Marcel Dekker Inc., New York.
Parham, P., J Immunol. 131 (1983) 2895-2902.
Parham, P., 1986, p. 14.1-14.23. In: D. M. Weir (Ed.), Handbook of Experimental Immunology, 4th Ed. Blackwell Scientific Publications, Oxford.
Porter, R. R., Biochem J. 73 (1959) 119-126.
Nisonoff, A., et al., Arch. Biochem. Biophys. 89 (1960) 230-244.
Zhao, Y. L., et al., Protein Expr. Purif 67 (2009) 182-189.
Akita, E. M., and S. Nakai, J. Immunol. Methods 162 (1993) 155-164.
Tischer, W. and V. Kasche, Trends Biotechnol. 17 (1999) 326-335.
Luo, Q., et al., J. Chrom. 776 (2002) 139-147.
von Pawel-Rammingen, U., et al., EMBO J. 21 (2002) 1607-1615.
von Pawel-Rammingen, U. and L. Bjorck, Curr. Opin. Microbiol. 6 (2003) 50-55.
Ishikawa, E. and S. Yoshitake, J. Immunol. Methods 38 (1980) 117-123.
DeSilva, B. S. and G. S. Wilson, G. S., J. Immunol. Methods 188 (1995) 9-19.
Billah, M. M., ET AL., Bioelectrochem. 80 (2010) 49-54.
Persson, H., ET AL., Infect. Immun. 81 (2013) 2236-2241.

The following examples and figures are provided to aid the understanding of the present invention, the true scope of which is set forth in the appended claims. It is understood that modifications can be made in the procedures set forth without departing from the spirit of the invention.

EXAMPLES

Figure 1:
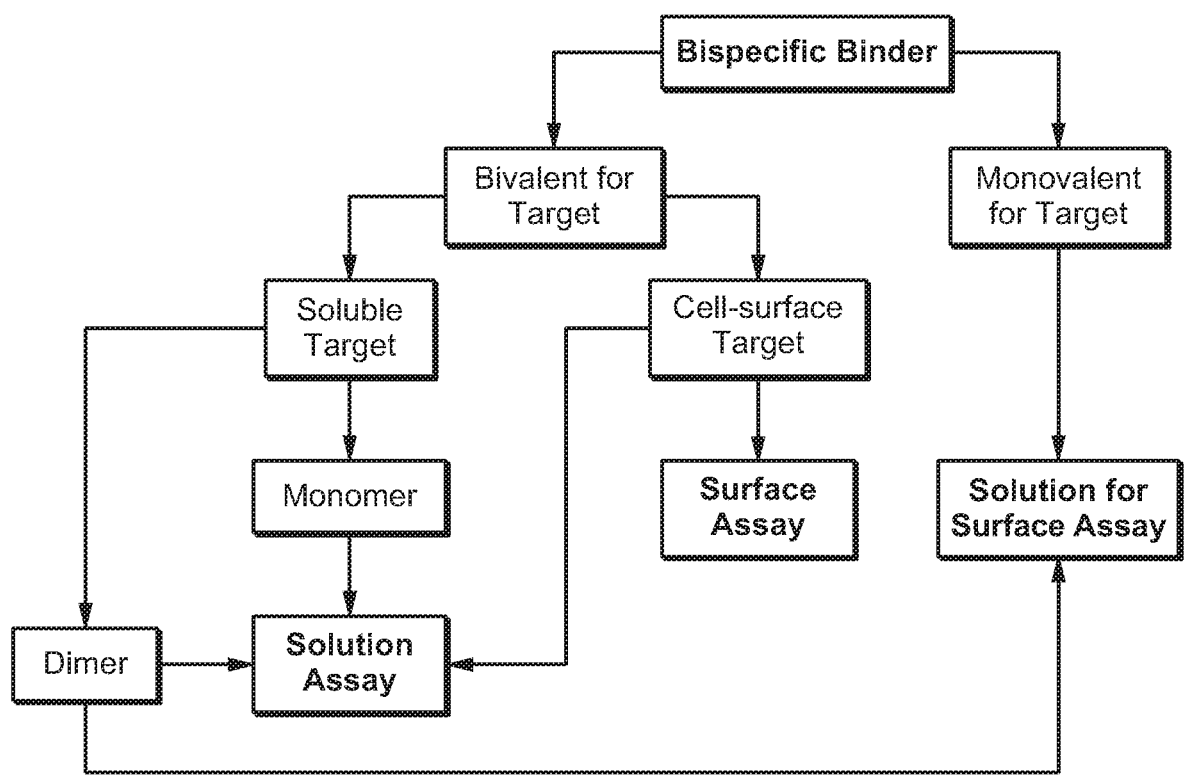
FIG. 1 Decision tree.
Figure 2:
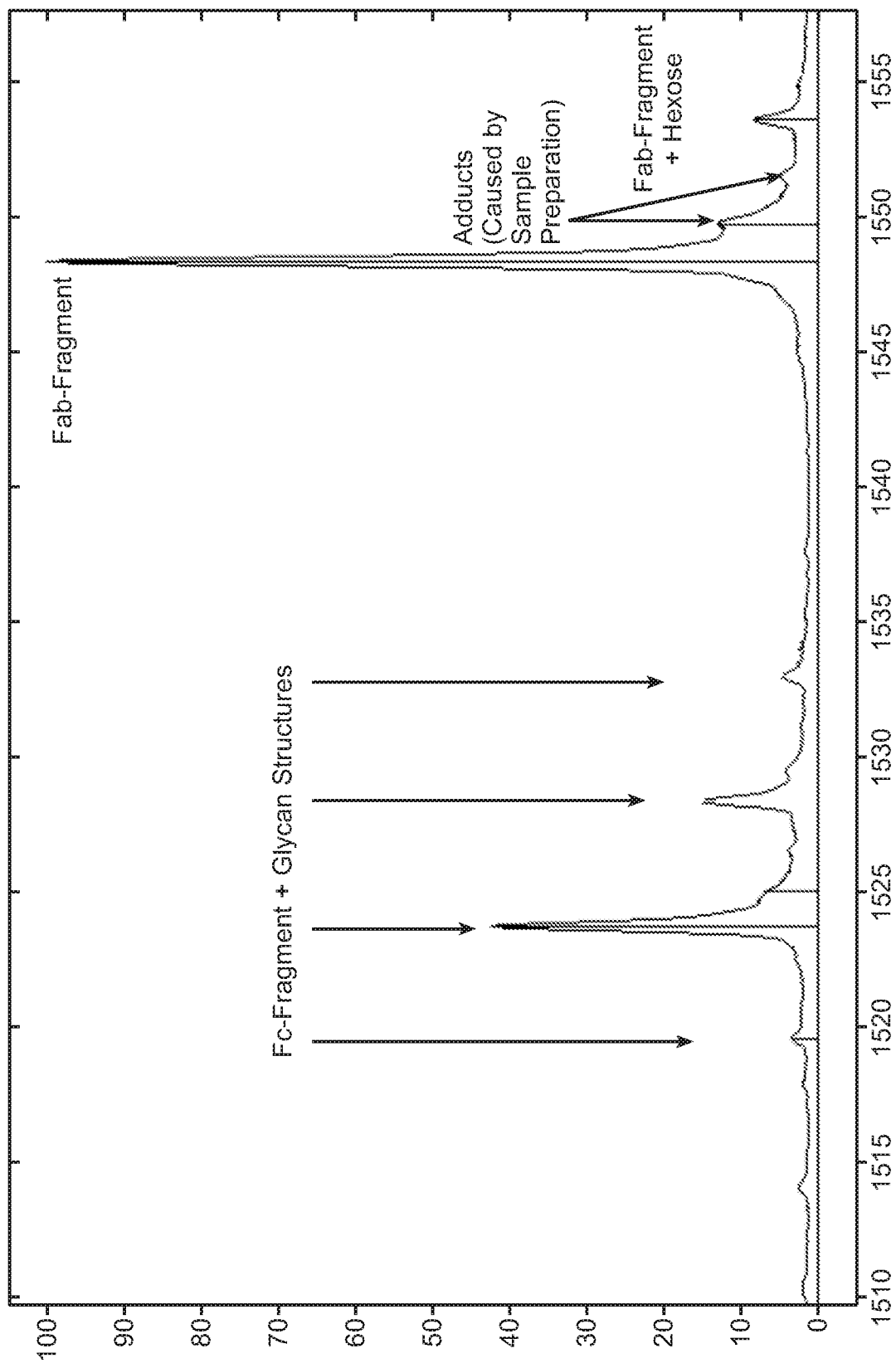
FIG. 2 UHR ESI-QTOF mass spectrometry of bevacizumab digested with lysine-gingipain of *Porphyromonas gingivalis* for one hour at 37° C. Only Fab and Fc fragments were detected.
Figure 3:
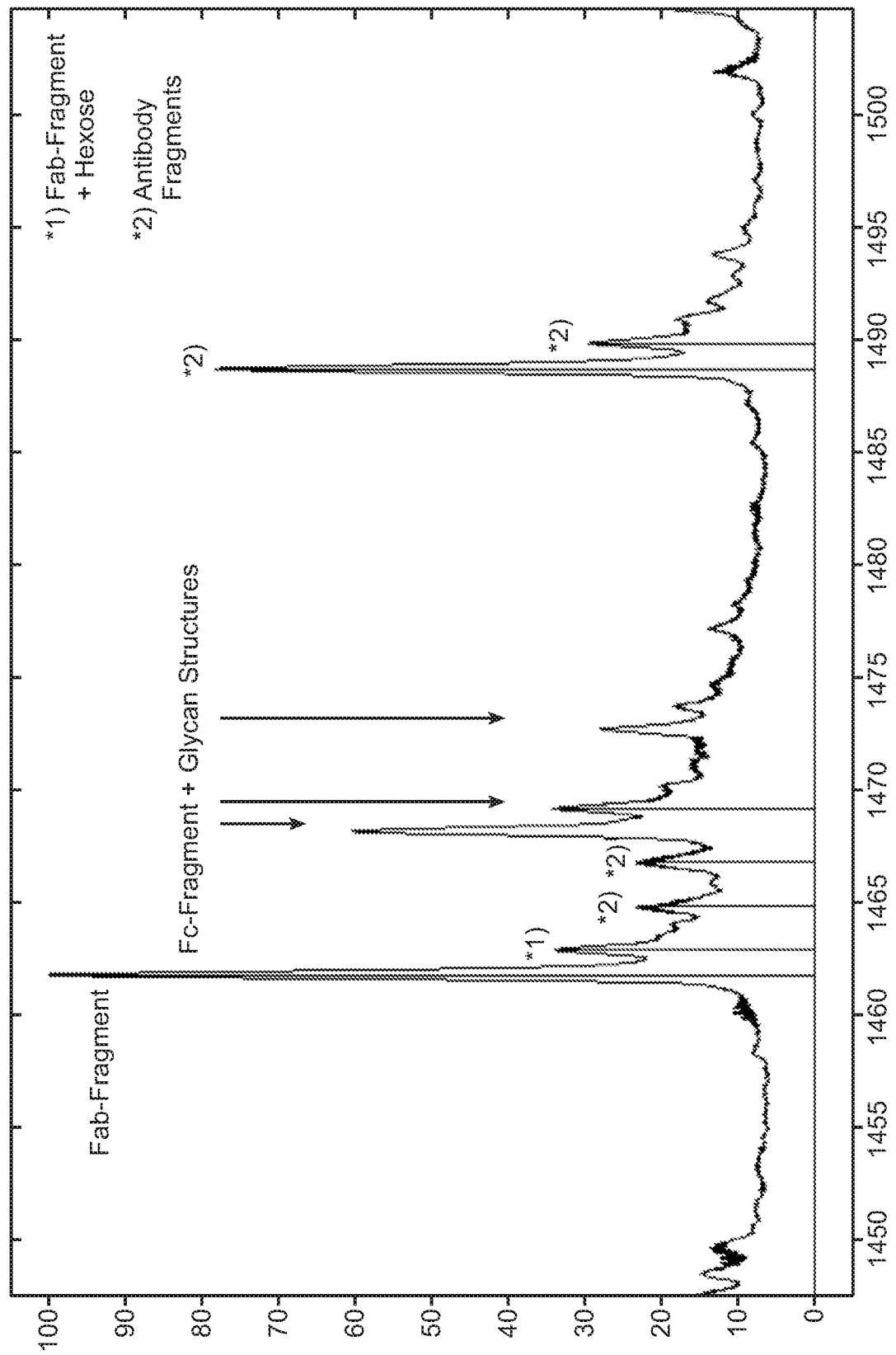
FIG. 3 UHR ESI-QTOF mass spectrometry of bevacizumab digested with papain for 1.5 h at 37° C. Beside Fab and Fc fragments, several Fab- and antibody fragments were detected.
Figure 4:
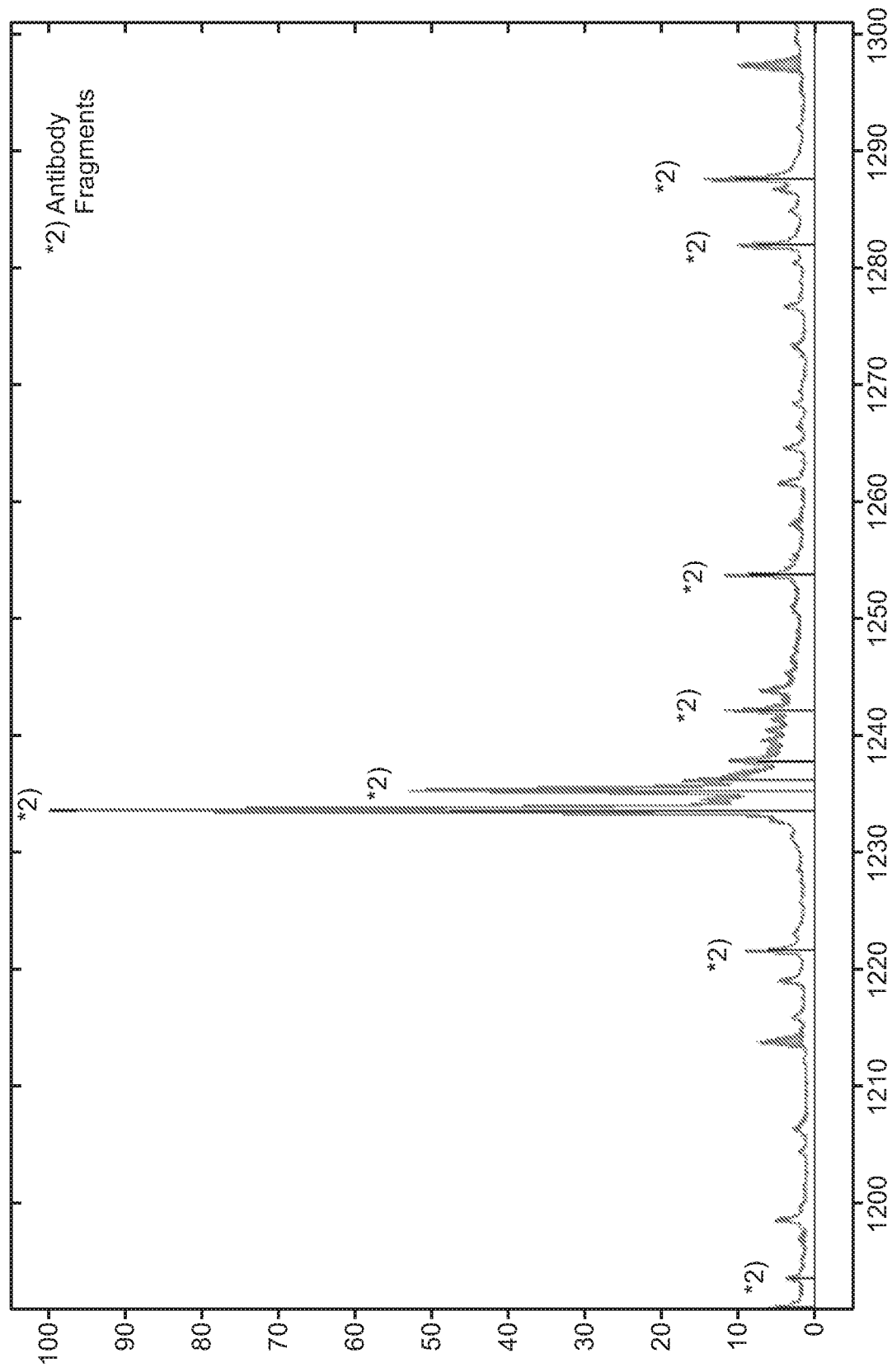
FIG. 4 UHR ESI-QTOF mass spectrometry of bevacizumab digested with papain for 2 h at 37° C. Several antibody fragments were detected. Fab and Fc fragment could not be identified.
Figure 5A:
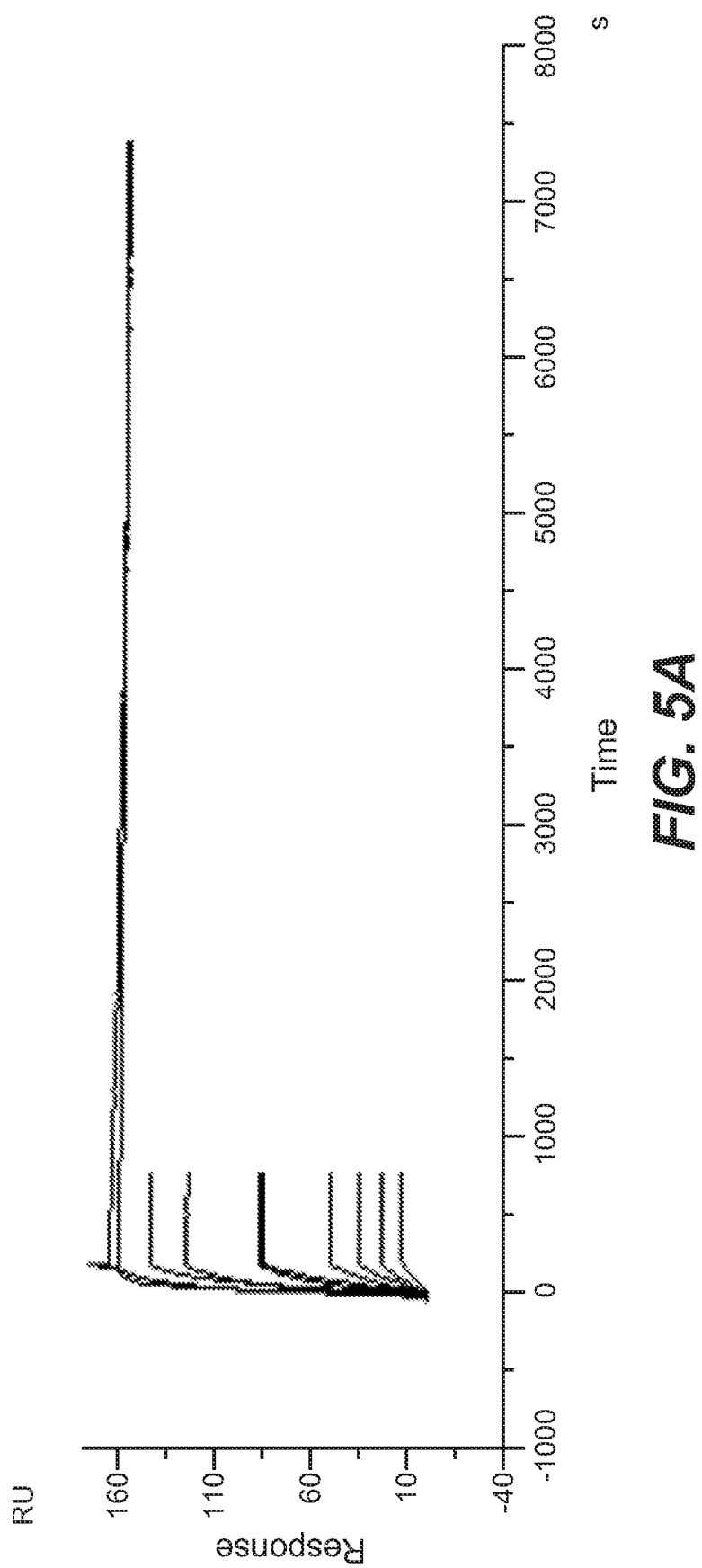
FIG. 5A Surface plasmon resonance sensorgrams of bevacizumab.
Figure 5B:
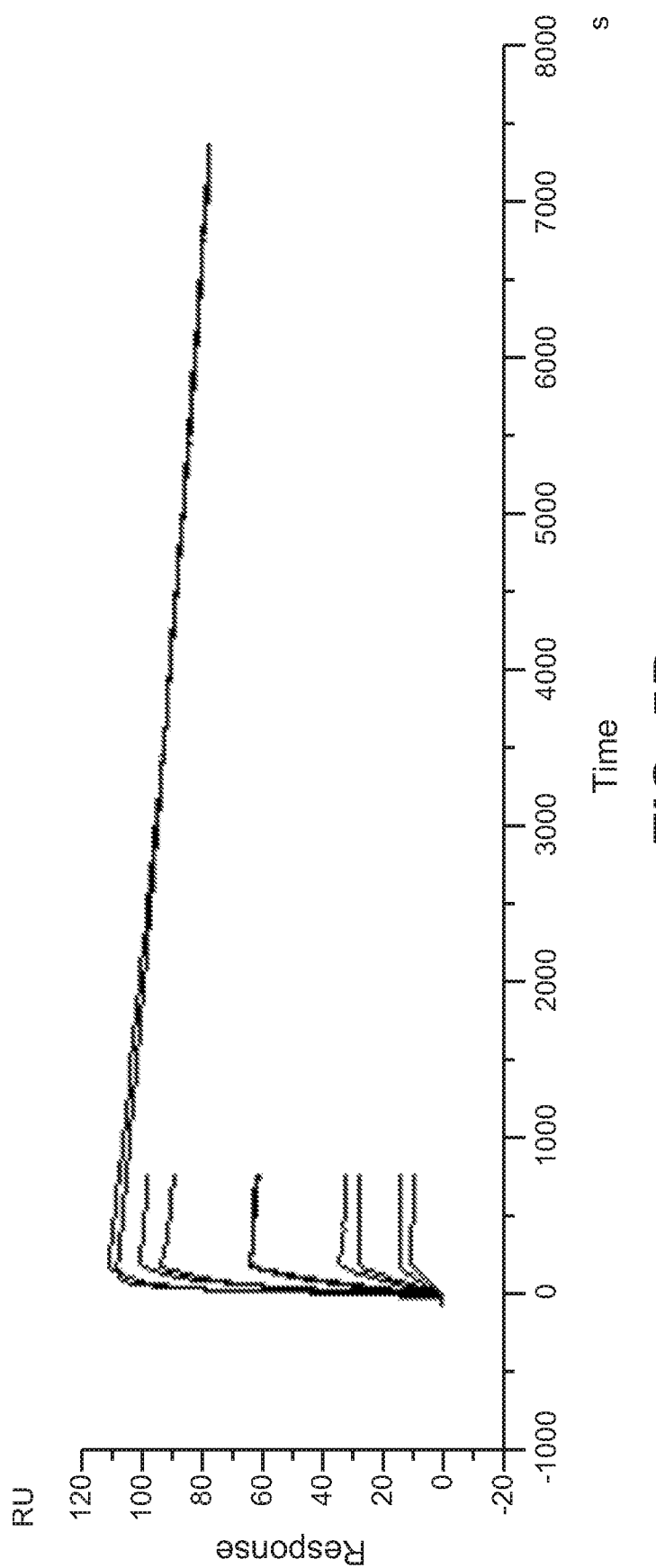
FIG. 5B Surface plasmon resonance sensorgrams of a recombinant bevacizumab Fab.
Figure 5C:
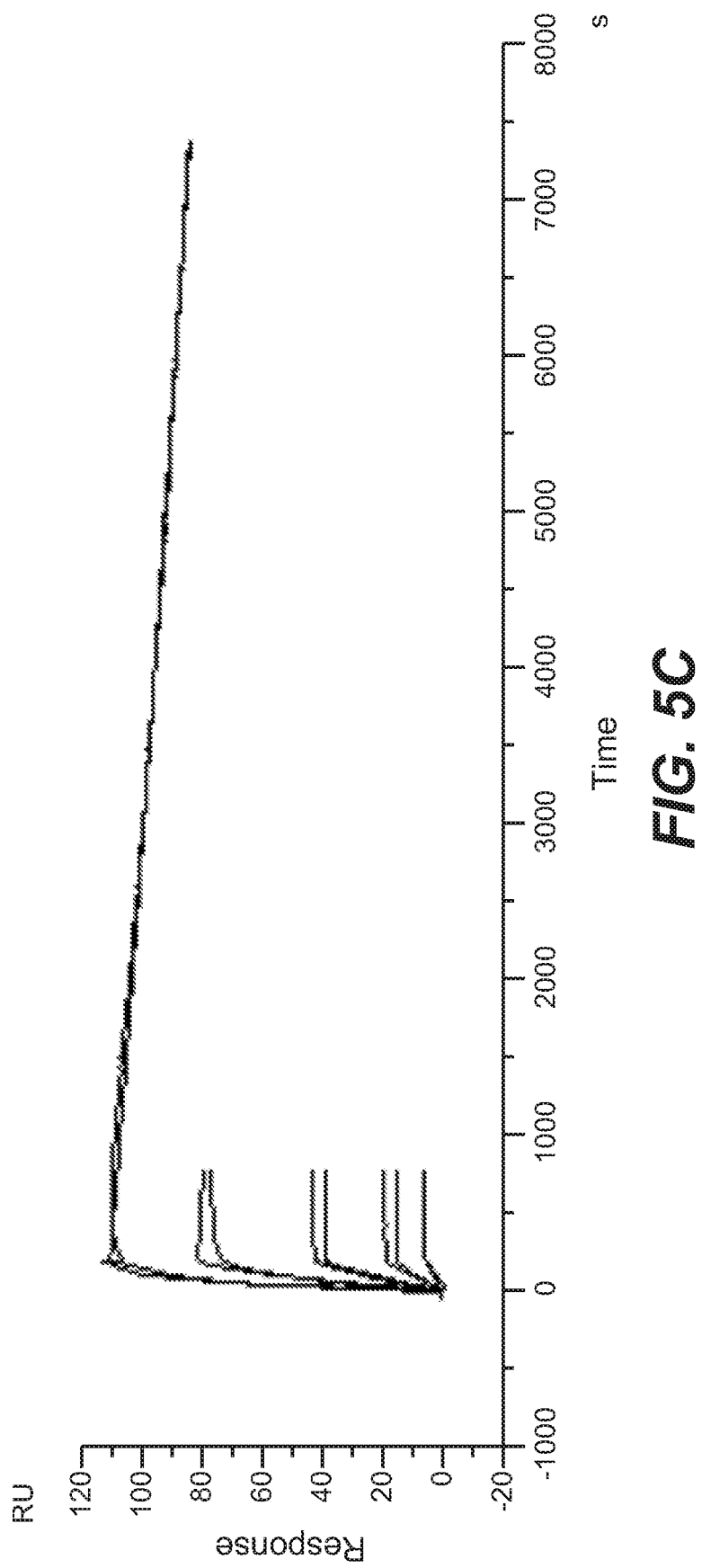
FIG. 5C Surface plasmon resonance sensorgrams of bevacizumab digested with lysine-gingipain of *Porphyromonas gingivalis*.
Figure 5D:
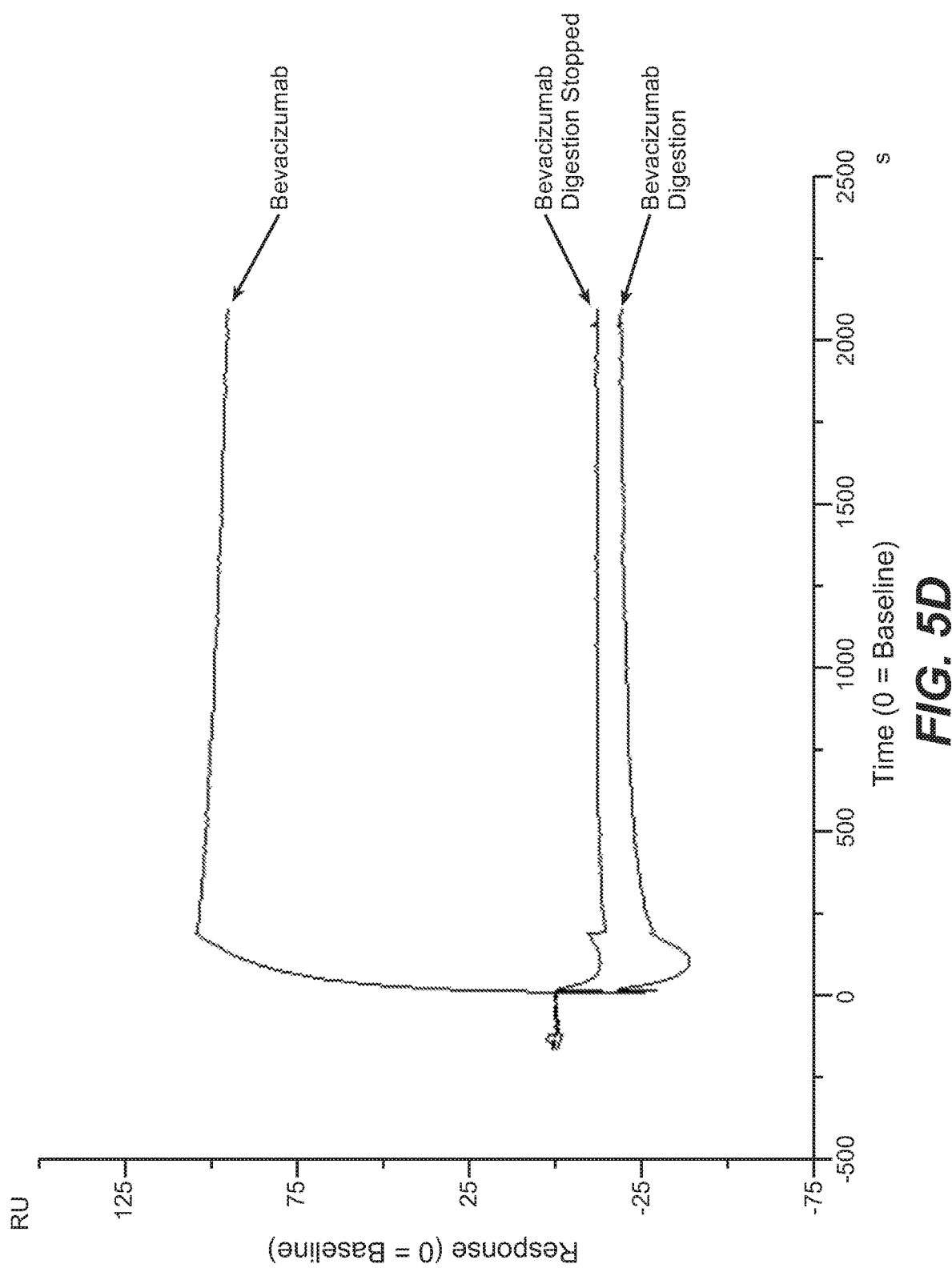
FIG. 5D Surface plasmon resonance sensorgrams of bevacizumab, bevacizumab digested with papain without termination of the digest, and bevacizumab digested with papain with termination of the digest.
Figure 6:
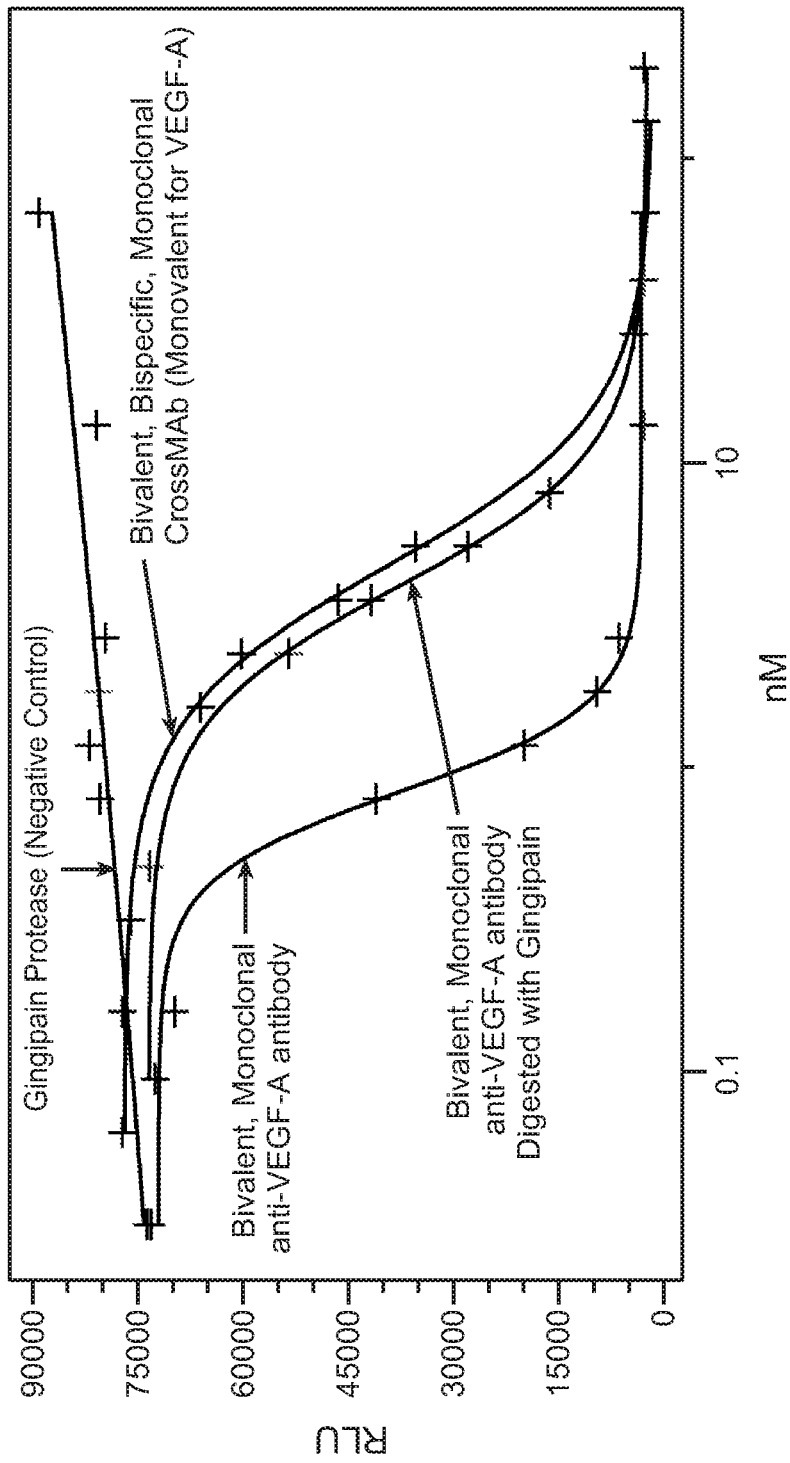
FIG. 6 Results of the analysis of the participation of a second binding site to target binding for the in vivo interaction mode.
Figure 7:
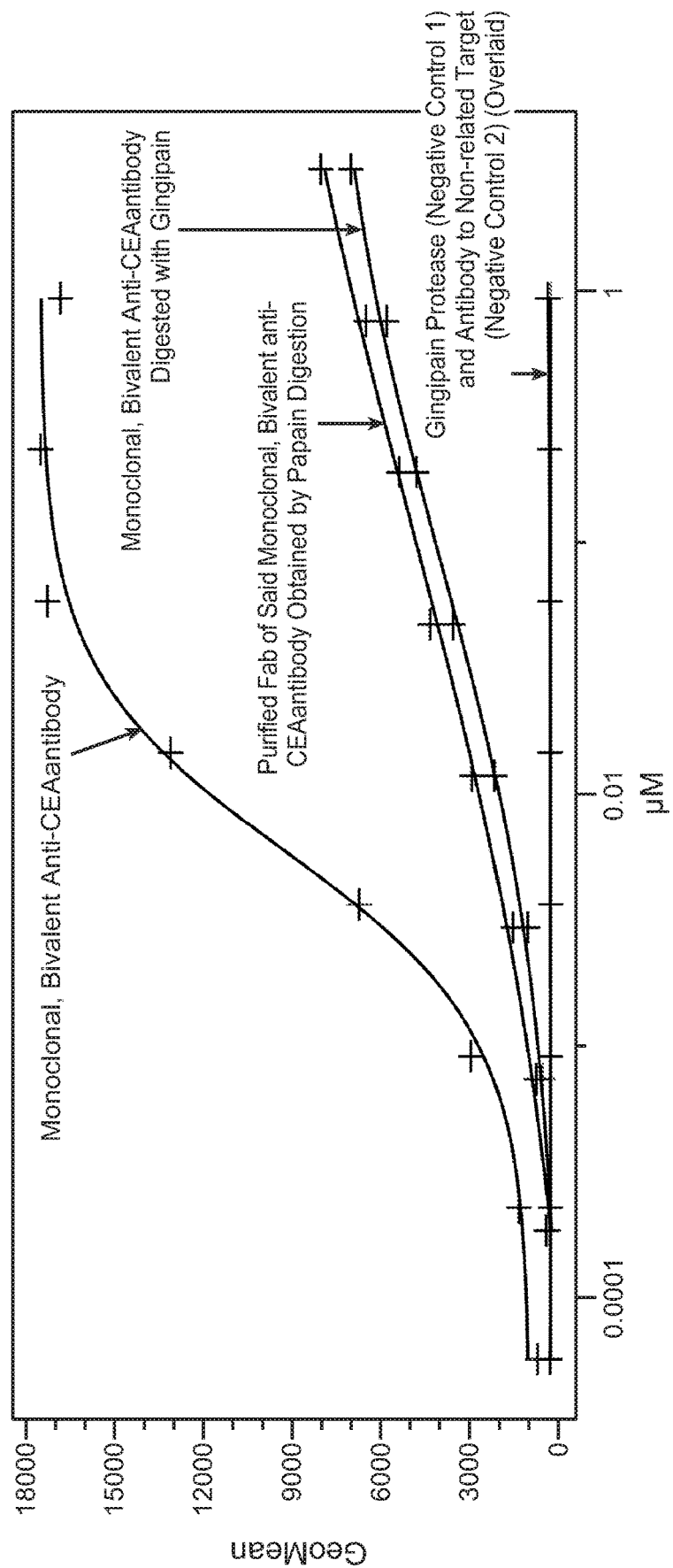
FIG. 7 Results of the analysis of the participation of a second binding site to target binding for the in vivo interaction mode.

Bevacizumab was obtained from Roche Diagnostics GmbH (Mannheim, Germany). Papain was obtained as suspension with a concentration of 10 mg/mL from Sigma-Aldrich/Roche Diagnostics GmbH. Lysine-gingipain of *Porphyromonas gingivalis* was obtained under the trade name GingisKHAN from Genovis (Lund, Sweden). GingisKHAN was reconstituted in 200 μL double distilled water (ddH2O) resulting in 2000 U/200 μL, and the 10× reducing agent was freshly prepared in 50 μL ddH2O (final concentration: 20 mM cysteine) prior to each digestion.

Example 1

Transient Fab Expression and Purification

The antibody light chain and heavy chain Fd-fragments were ordered as gene syntheses and cloned via unique restriction sites using standard cloning procedures into separate expression vectors for each chain enabling secretory expression in HEK cells growing in suspension. Transfection (1:1 plasmid ratios) into HEK293-F cells (Invitrogen, Cat. No. 510029) was performed according to the cell supplier's instructions using Maxiprep (Qiagen, Cat. No. 12163) preparations of the antibody vectors, Opti-MEM I medium (Invitrogen, Cat. No. 31985) 293fectin (Invitrogen, Cat. No. 31985070), and an initial cell density of 1-2×10E+06 viable cells/mL in serum-free FreeStyle 293 expression medium (Invitrogen, Cat. No. 12338018). Antibody containing cell culture supernatants were harvested after 7 days of cultivation in shake flasks by centrifugation at 14,000×g for 30 min. and filtered through a 0.22 μm sterile filter (Thermo Scientific, Cat. No. 566-0020). The antibodies were purified directly from the supernatant, or the supernatant was stored at −80° C. until purification. The quality of the purified Fab was analyzed by SEC and BioAnalyzer.

Example 2

Enzymatic Cleavage of Bevacizumab with Papain
Without Purification:

The antibody was diluted in 20 mM Histidine, 140 mM NaCl, pH 6.0 to a final concentration of 1 mg/mL, added 2 μL 250 mM L-cysteine (Sigma-Aldrich, Schnelldorf, Germany) and 10.9 μL diluted papain (7.34 U/mL in 20 mM Histidine, 140 mM NaCl, pH 6.0), and incubated 1 h at 37° C.

With Purification:

The antibody was incubated with Papain (0.8 U/mg mAb; Sigma-Aldrich/Roche) in presence of 5 mM Cystein for 170 minutes at 37° C. To isolate the Fab from non-cleaved antibodies, Fc-fragments and Papain, the mixture was applied to a CaptureSelect IgG-CH1 and MabSelectSuRe affinity chromatography (GE Healthcare) according to manufacturer protocol. Finally, a size exclusion chromatography using a Superdex 75 10/300 GL column (GE Healthcare) was performed using 140 mM NaCl, 20 mM histidine (pH 6.0) as running buffer. Protein concentration of the Fab was determined by measuring the optical density (OD) at 280 nm, using the molar extinction coefficient calculated on the basis of the amino acid sequence. The purity was analyzed by SDS-PAGE in the presence and absence of a reducing agent (5 mM 1,4-dithiotreitol) and staining with Coomassie brilliant blue.

Example 3

Enzymatic Cleavage of Bevacizumab with Lysine-Gingipain of *Porphyromonas gingivalis*

GingisKHAN was reconstituted in 200 μL ddH2O resulting in 2000 U/200 μL, and the 10× reducing agent was freshly prepared in 50 μL ddH2O (final concentration: 20 mM Cysteine) prior to each digestion. 100 μg antibody was diluted to a final concentration of 1 mg/mL in 100 mM Tris, pH 8.0 and subsequently digested with 10 μL GingisKHAN and 11 μL of freshly prepared 10× reducing agent at 37° C. for 1 hour.

Example 4

UHR-ESI-QTOF Mass Spectrometry

Samples were desalted by HPLC on a Sephadex G25 column (Kronlab, 5×250 mm, TAC05/250G0-SR) using 40% acetonitrile with 2% formic acid (v/v). The total mass was determined via ESI-QTOF MS on a maXis 4G UHR-QTOF MS system (Bruker Daltonik) equipped with a Tri-Versa NanoMate source (Advion). Calibration was performed with sodium iodide (Waters ToF G2-Sample Kit 2 Part: 700008892-1). For the recombinant and purified Fabs, data acquisition was done at 900-2600 m/z (ISCID: 0.0 eV), for the hIgG1s or digested hIgG1s, data acquisition was done at 900-4000 m/z (ISCID: 0.0 eV). The raw mass spectra were evaluated and transformed into individual relative molar masses using an in-house developed Roche software tool. For visualization of the results, the same in-house developed software was used to generate deconvoluted mass spectra.

Example 5

Surface Plasmon Resonance

Binding affinities and kinetics were investigated by surface plasmon resonance using a BIACORE™ T200 instrument (GE Healthcare). All experiments were performed at 25° C. using PBS-T (10 mM Na2HPO4, 140 mM NaCl, 0.05% TWEEN® 20, pH 7.4) as running and dilution buffer. An anti-His-tag (GE Healthcare, #28995056) or an anti-human Fab antibody (GE Healthcare, #28958325) was immobilized on a Series S CM5 Sensor Chip (GE Healthcare, #29104988) using standard amine coupling chemistry. Histidine-tagged human VEGF or full length IgG/Fabs were captured on the surface leading to a response between 10 and 50 RU. The analytes were injected for 180 s at concentrations from 2.2 nM up to 1800 nM onto the surface (association phase) at a flow rate of 30 µL/min. The dissociation phase was monitored for up to 3600 seconds by washing with running buffer. The surface was regenerated by injecting 10 mM Glycine pH 1.5 for 60 seconds at a flow rate of 5 µL/min. Bulk refractive index differences were corrected by subtracting the response obtained from a mock surface and by subtracting blank injections (double referencing). The derived curves were fitted to a 1:1 Langmuir binding model using the BIAevaluation software.

Example 6

VEGF-A Specific Reporter Gene Assay

A reporter gene cell line GloResponse™ NFAT-RE-luc2P/KDR HEK293 expressing KDR (KDR=VEGF receptor 2) and a NFAT responsive element in front of the firefly luciferase was purchased from Promega Corporation, Madison, USA. Upon binding of VEGF-A to the KDR a signal transduction via Calcineurin results in activation of NFAT, translocation to the nucleus, binding to the NFAT responsive element and subsequently expression of the luciferase gene. VEGF121 (10.8 nM 40 µL/well) was incubated with the anti-VEGF antibody, said antibody digested with lysine-gingipain of Porphyromonas gingivalis, a bispecific anti-VEGF-A/second, non-related antigen CrossMab, and a negative lysine-gingipain of Porphyromonas gingivalis control (diluted in DMEM, 1% FBS, 40 µL/well) for approximately 30 min. at room temperature. $5 \times 10^4$ GloResponse™ HEK293 cells (Promega Coop., cultured in FreeStyle™ 293 Expression Medium, 100 µg/mL Hygromycin B, 250 µg/mL Geneticin (Thermo Fischer Scientific, Sigma-Aldrich, Calbiochem) in 40 µL DMEM, supplemented with 1% FBS, were added as suspension and incubated for 5 hours at 37° C., 5% $CO_2$. The plate was equilibrated at room temperature for approximately 15 min. before the luminescence substrate (Promega Coop., ONE-Glo™ EX, 60 µL/well) was added. The contents were mixed on an orbital shaker for about 1-3 min. at 600 rpm. The luminescence intensity was measured with a luminescence reader.

Example 7

CEACAM5 Cell Surface Binding Assay $1 \times 10^5$ gastric adenocarcinoma cells cultured in RPMI1640, 20% fetal bovine serum (FBS), 1× GIBCO GlutaMax (Thermo Fischer Scientific, Dreieich, Germany) were washed twice with PBS, 5% FBS, resuspended in PBS, 5% FBS and incubated with the anti-CEA antibody, a purified Fab fragment obtained by papain digestion of said anti-CEA antibody, said antibody digested with lysine-gingipain of Porphyromonas gingivalis and negative controls (an antibody binding to a non-related target, lysine-gingipain of Porphyromonas gingivalis only) for one hour at 4° C. Bound antibodies/Fab fragments were detected using a mouse anti-human kappa light chain antibody (150 µg/mL) labeled using the Alexa Fluor 647 Protein Labeling Kit according to the instructions of the manufacturer (Molecular Probes, Thermo Fischer Scientific). The mixture was incubated in the dark at 4° C. for 30 min. and analyzed by flow cytometry using a BD FACSCanto II and the FACSDiva Software (BD Biosciences, Heidelberg, Germany). The specificity was verified with an isotype control (Alexa Fluor 647-labelled mouse IgG2a, BD Biosciences). Gating of viable cells was done using forward and sideward scatter based on size and granularity, and the bound antibody/Fab fragment was detected by measuring the fluorescence signal.

What is claimed is:

1. A method for determining the binding interaction with a multimeric antigen of an antibody of the human class G immunoglobulin, subclass 1 (IgG1) comprising the following steps:
   1) determining the binding affinity of the antibody for the multimeric antigen,
   2) incubating a mixture comprising the antibody, the multimeric antigen and lysine-gingipain of *Porphyromonas gingivalis* at a pH of 7.5 to 8.5, in the presence of a reducing agent, at a temperature of 30° C. to 42° C., for a time of 10 minutes to 240 minutes to cleave the antibody into antigen-binding fragments (Fabs) and a crystallizing fragment (Fc)-region, whereby the concentration of the antibody prior to said cleaving is higher than the concentration of the antigen, and determining the binding affinity of the Fabs of the antibody for the multimeric antigen,
   and
   3) determining the binding affinity of the antibody to the multimeric antigen to be affinity-driven if the binding affinity determined in step 1) and 2) is comparable and to be avidity-driven if the binding affinity determined in both step 1) and 2) is different;
   wherein the binding affinity is determined in solution using an enzyme-linked immunosorbent assay (ELISA) or a surface plasmon resonance method; and
   wherein the binding affinities determined in steps 1 and 2 of the antibody to the multimeric antigen are comparable if the binding affinities determined in both steps differ by a factor of 2 or less, wherein the smaller value is used as basis for the calculation; and is different if the binding affinities determined in both steps differ by more than a factor of 2, wherein the smaller value is set to 100%.

2. A method for selecting the assay format for determining the binding interaction of an antibody of the human IgG1 subclass with a multimeric antigen comprising the following steps:
   1) determining the binding affinity of the antibody for the multimeric antigen using a surface plasmon resonance method,
   2) incubating a mixture comprising the antibody, the antigen and lysine-gingipain of *Porphyromonas gingivalis* at a pH of 7.5 to 8.5, in the presence of a reducing agent, at a temperature of 30° C. to 42° C., for a time of 10 mift. minutes to 240 mift. minutes to cleave the antibody into Fabs and g Fe-region, whereby the concentration of the antibody prior to said cleaving is higher than the concentration of the antigen, and determining the binding affinity of the Fabs of the antibody for their antigen using surface plasmon resonance by directly applying the incubated reaction mixture obtained in the previous step in the surface plasmon resonance method,
   whereby the binding affinity of the antibody to the multimeric antigen is i) affinity-driven if the binding affinity determined in step 1) and 2) is comparable, or ii) avidity-driven if the binding affinity determined in step 1) and 2) is different,
   and
   selecting
   i) in case of an affinity-driven interaction with a soluble multimeric antigen a solution assay,
   ii) in case of an avidity-driven interaction with a soluble multimeric antigen a solution or a surface assay,
   iii) in case of an affinity-driven interaction with a surface bound antigen a solution assay, or
   iv) in case of an avidity-driven interaction with a surface bound antigen a surface assay for determining the binding interaction of the antibody of the human IgG 1 subclass with the multimeric antigen;
   wherein the binding affinity is determined in solution using an ELISA or a surface plasmon resonance method; and
   wherein the binding affinities determined in steps 1 and 2 of the antibody to the multimeric antigen are comparable if the binding affinities determined in both steps differ by a factor of 2 or less, wherein the smaller value is used as basis for the calculation; and is different if the binding affinities determined in both steps differ by more than a factor of 2, wherein the smaller value is set to 100%.

3. The method according to claim 1, wherein the binding affinity is determined using a cellular assay using fluorescence-activated cell sorting (FACS) or a cellular effect.

4. The method according to claim 1, wherein the binding affinity is determined with an antibody:multimeric antigen ratio of 10 or more.

5. The method according to claim 1, wherein the polypeptide that is derived from lysine-gingipain of *Porphyromonas gingivalis* is the lysine-gingipain of *Porphyromonas gingivalis*.

6. The method according to claim 5, wherein the polypeptide that is derived from lysine-gingipain of *Porphyromonas gingivalis* comprises the amino acid sequence of SEQ ID NO: 02, SEQ ID NO: 03, SEQ ID NO: 04.

7. The method according to claim 5, wherein the polypeptide that is derived from lysine-gingipain of *Porphyromonas gingivalis* has an amino acid sequence that comprises at least residues 230 to 739 of SEQ ID NO: 01.

8. The method according to claim 1, wherein the reducing agent is selected from the group consisting of 2-mercaptoethanol, cysteine, and dithiothreitol.

9. The method according to claim 8, wherein the reducing agent is cysteine.

10. The method according to claim 8, wherein the reducing agent is cysteine at a concentration of from 0.5 mM to 10 mM.

11. The method according to claim 1, wherein the pH value is about pH 8.

12. The method according to claim 1, wherein the temperature is of from 35° C. to 38° C.

13. The method according to claim 1, wherein the incubating is for a time of about 60 minutes.

14. The method according to claim 1, wherein the incubated mixture is used for the determination of the binding affinity without intermediate purification.

15. The method according to claim 1, wherein the determining of the binding affinity is by surface plasmon resonance.

16. The method according to claim 4, wherein the incubated mixture is used for the determination of the binding affinity without intermediate purification.

17. The method according to claim 16, wherein the determining of the binding affinity is by surface plasmon resonance.

18. The method according to claim 2, wherein the incubated mixture is used for the determination of the binding affinity without intermediate purification.

19. The method according to claim 18, wherein the determining of the binding affinity is by surface plasmon resonance.

20. The method according to claim 19, wherein the binding affinities determined in steps 1) and 2) of the antibody to the multimeric antigen are comparable if the binding affinities determined in both steps differ by a factor of 2 or less, wherein the smaller value is used as basis for the calculation, and is different if the binding affinities determined in both steps differ by more than a factor of 2, wherein the smaller value is set to 100%.

21. The method according to claim 17, wherein the binding affinity is determined with an antibody:multimeric antigen ratio of 10 or more.

22. The method according to claim 20, wherein the binding affinity is determined with an antibody:multimeric antigen ratio of 10 or more.

23. The method according to claim 21, wherein the polypeptide that is derived from lysine-gingipain of *Porphyromonas gingivalis* is the lysine-gingipain of *Porphyromonas gingivalis*.

24. The method according to claim 22, wherein the polypeptide that is derived from lysine-gingipain of *Porphyromonas gingivalis* is the lysine-gingipain of *Porphyromonas gingivalis*.

25. The method according to claim 23, wherein the polypeptide that is derived from lysine-gingipain of *Porphyromonas gingivalis* comprises the amino acid sequence of SEQ ID NO: 02, SEQ ID NO: 03, SEQ ID NO: 04.

26. The method according to claim 6, wherein the polypeptide that is derived from lysine-gingipain of *Porphyromonas gingivalis* comprises the amino acid sequence of SEQ ID NO: 02, SEQ ID NO: 03, SEQ ID NO: 04.

27. The method according to claim 6, wherein the reducing agent is selected from the group consisting of 2-mercaptoethanol, cysteine, and dithiothreitol.

28. The method according to claim 25, wherein the reducing agent is selected from the group consisting of 2-mercaptoethanol, cysteine, and dithiothreitol.

29. The method according to claim 26, wherein the reducing agent is selected from the group consisting of 2-mercaptoethanol, cysteine, and dithiothreitol.

30. The method according to claim 27, wherein the reducing agent is cysteine at a concentration of from 0.5 mM to 10 mM.

31. The method according to claim 28, wherein the reducing agent is cysteine at a concentration of from 0.5 mM to 10 mM.

32. The method according to claim 29, wherein the reducing agent is cysteine at a concentration of from 0.5 mM to 10 mM.

33. The method according to claim 1, wherein said multimeric antigen is vascular endothelial growth factor-A (VEGF-A), angiopoietin-2 (ANG2) or fibroblast activation protein (FAP).

34. The method according to claim 2, wherein said multimeric antigen is vascular endothelial growth factor-A (VEGF-A), angiopoietin-2 (ANG2) or fibroblast activation protein (FAP).

* * * * *

SEQUENCE LISTING

```
<160> NUMBER OF SEQ ID NOS: 7

<210> SEQ ID NO 1
<211> LENGTH: 1733
<212> TYPE: PRT
<213> ORGANISM: Porphyromonas gingivalis

<400> SEQUENCE: 1

Met Arg Lys Leu Leu Leu Leu Ile Ala Ala Ser Leu Leu Gly Val Gly
1               5                   10                  15

Leu Tyr Ala Gln Ser Ala Lys Ile Lys Leu Asp Ala Pro Thr Thr Arg
            20                  25                  30

Thr Thr Cys Thr Asn Asn Ser Phe Lys Gln Phe Asp Ala Ser Phe Ser
        35                  40                  45

Phe Asn Glu Val Glu Leu Thr Lys Val Glu Thr Lys Gly Gly Thr Phe
    50                  55                  60

Ala Ser Val Ser Ile Pro Gly Ala Phe Pro Thr Gly Glu Val Gly Ser
65                  70                  75                  80

Pro Glu Val Pro Ala Val Arg Lys Leu Ile Ala Val Pro Val Gly Ala
                85                  90                  95
```

-continued

Thr Pro Val Val Arg Val Lys Ser Phe Thr Glu Gln Val Tyr Ser Leu
            100                 105                 110

Asn Gln Tyr Gly Ser Glu Lys Leu Met Pro His Gln Pro Ser Met Ser
            115                 120                 125

Lys Ser Asp Asp Pro Glu Lys Val Pro Phe Val Tyr Asn Ala Ala Ala
            130                 135                 140

Tyr Ala Arg Lys Gly Phe Val Gly Gln Glu Leu Thr Gln Val Glu Met
145                 150                 155                 160

Leu Gly Thr Met Arg Gly Val Arg Ile Ala Ala Leu Thr Ile Asn Pro
            165                 170                 175

Val Gln Tyr Asp Val Val Ala Asn Gln Leu Lys Val Arg Asn Asn Ile
            180                 185                 190

Glu Ile Glu Val Ser Phe Gln Gly Ala Asp Glu Val Ala Thr Gln Arg
            195                 200                 205

Leu Tyr Asp Ala Ser Phe Ser Pro Tyr Phe Glu Thr Ala Tyr Lys Gln
            210                 215                 220

Leu Phe Asn Arg Asp Thr Val Tyr Thr Asp His Gly Asp Leu Tyr Asn
225                 230                 235                 240

Thr Pro Val Arg Met Leu Val Val Ala Gly Ala Lys Phe Lys Glu Ala
            245                 250                 255

Leu Lys Pro Trp Leu Thr Trp Lys Ala Gln Lys Gly Phe Tyr Leu Asp
            260                 265                 270

Val His Tyr Thr Asp Glu Ala Glu Val Gly Thr Thr Asn Ala Ser Ile
            275                 280                 285

Lys Ala Phe Ile His Lys Lys Tyr Asn Asp Gly Leu Ala Ala Ser Ala
            290                 295                 300

Ala Pro Val Phe Leu Ala Leu Val Gly Asp Thr Asp Val Ile Ser Gly
305                 310                 315                 320

Glu Lys Gly Lys Lys Thr Lys Lys Val Thr Asp Leu Tyr Tyr Ser Ala
            325                 330                 335

Val Asp Gly Asp Tyr Phe Pro Glu Met Tyr Thr Phe Arg Met Ser Ala
            340                 345                 350

Ser Ser Pro Glu Glu Leu Thr Asn Ile Ile Asp Lys Val Leu Met Tyr
            355                 360                 365

Glu Lys Ala Thr Met Pro Asp Lys Ser Tyr Leu Glu Lys Val Leu Leu
            370                 375                 380

Ile Ala Gly Ala Asp Tyr Ser Trp Asn Ser Gln Val Gly Gln Pro Thr
385                 390                 395                 400

Ile Lys Tyr Gly Met Gln Tyr Tyr Asn Gln Glu His Gly Tyr Thr
            405                 410                 415

Asp Val Tyr Asn Tyr Leu Lys Ala Pro Tyr Thr Gly Cys Tyr Ser His
            420                 425                 430

Leu Asn Thr Gly Val Ser Phe Ala Asn Tyr Thr Ala His Gly Ser Glu
            435                 440                 445

Thr Ala Trp Ala Asp Pro Leu Leu Thr Thr Ser Gln Leu Lys Ala Leu
            450                 455                 460

Thr Asn Lys Asp Lys Tyr Phe Leu Ala Ile Gly Asn Cys Cys Ile Thr
465                 470                 475                 480

Ala Gln Phe Asp Tyr Val Gln Pro Cys Phe Gly Glu Val Ile Thr Arg
            485                 490                 495

Val Lys Glu Lys Gly Ala Tyr Ala Tyr Ile Gly Ser Ser Pro Asn Ser
            500                 505                 510

-continued

```
Tyr Trp Gly Glu Asp Tyr Tyr Trp Ser Val Gly Ala Asn Ala Val Phe
            515                 520                 525

Gly Val Gln Pro Thr Phe Glu Gly Thr Ser Met Gly Ser Tyr Asp Ala
        530                 535                 540

Thr Phe Leu Glu Asp Ser Tyr Asn Thr Val Asn Ser Ile Met Trp Ala
545                 550                 555                 560

Gly Asn Leu Ala Ala Thr His Ala Gly Asn Ile Gly Asn Ile Thr His
                565                 570                 575

Ile Gly Ala His Tyr Tyr Trp Glu Ala Tyr His Val Leu Gly Asp Gly
            580                 585                 590

Ser Val Met Pro Tyr Arg Ala Met Pro Lys Thr Asn Thr Tyr Thr Leu
        595                 600                 605

Pro Ala Ser Leu Pro Gln Asn Gln Ala Ser Tyr Ser Ile Gln Ala Ser
    610                 615                 620

Ala Gly Ser Tyr Val Ala Ile Ser Lys Asp Gly Val Leu Tyr Gly Thr
625                 630                 635                 640

Gly Val Ala Asn Ala Ser Gly Val Ala Thr Val Ser Met Thr Lys Gln
                645                 650                 655

Ile Thr Glu Asn Gly Asn Tyr Asp Val Val Ile Thr Arg Ser Asn Tyr
            660                 665                 670

Leu Pro Val Ile Lys Gln Ile Gln Val Gly Glu Pro Ser Pro Tyr Gln
        675                 680                 685

Pro Val Ser Asn Leu Thr Ala Thr Thr Gln Gly Gln Lys Val Thr Leu
    690                 695                 700

Lys Trp Glu Ala Pro Ser Ala Lys Lys Ala Glu Gly Ser Arg Glu Val
705                 710                 715                 720

Lys Arg Ile Gly Asp Gly Leu Phe Val Thr Ile Glu Pro Ala Asn Asp
                725                 730                 735

Val Arg Ala Asn Glu Ala Lys Val Val Leu Ala Ala Asp Asn Val Trp
            740                 745                 750

Gly Asp Asn Thr Gly Tyr Gln Phe Leu Leu Asp Ala Asp His Asn Thr
        755                 760                 765

Phe Gly Ser Val Ile Pro Ala Thr Gly Pro Leu Phe Thr Gly Thr Ala
    770                 775                 780

Ser Ser Asn Leu Tyr Ser Ala Asn Phe Glu Tyr Leu Ile Pro Ala Asn
785                 790                 795                 800

Ala Asp Pro Val Val Thr Thr Gln Asn Ile Ile Val Thr Gly Gln Gly
                805                 810                 815

Glu Val Val Ile Pro Gly Gly Val Tyr Asp Tyr Cys Ile Thr Asn Pro
            820                 825                 830

Glu Pro Ala Ser Gly Lys Met Trp Ile Ala Gly Asp Gly Asn Gln
        835                 840                 845

Pro Ala Arg Tyr Asp Asp Phe Thr Phe Glu Ala Gly Lys Lys Tyr Thr
    850                 855                 860

Phe Thr Met Arg Arg Ala Gly Met Gly Asp Gly Thr Asp Met Glu Val
865                 870                 875                 880

Glu Asp Asp Ser Pro Ala Ser Tyr Thr Tyr Thr Val Tyr Arg Asp Gly
                885                 890                 895

Thr Lys Ile Lys Glu Gly Leu Thr Ala Thr Thr Phe Glu Glu Asp Gly
            900                 905                 910

Val Ala Ala Gly Asn His Glu Tyr Cys Val Glu Val Lys Tyr Thr Ala
        915                 920                 925

Gly Val Ser Pro Lys Val Cys Lys Asp Val Thr Val Glu Gly Ser Asn
```

```
                930             935             940
Glu Phe Ala Pro Val Gln Asn Leu Thr Gly Ser Ser Val Gly Gln Lys
945                 950             955                 960

Val Thr Leu Lys Trp Asp Ala Pro Asn Gly Thr Pro Asn Pro Asn Pro
                965             970             975

Asn Pro Asn Pro Asn Pro Gly Thr Thr Leu Ser Glu Ser Phe Glu Asn
            980             985             990

Gly Ile Pro Ala Ser Trp Lys Thr Ile Asp Ala Asp Gly Asp Gly His
        995             1000            1005

Gly Trp Lys Pro Gly Asn Ala Pro Gly Ile Ala Gly Tyr Asn Ser
    1010            1015            1020

Asn Gly Cys Val Tyr Ser Glu Ser Phe Gly Leu Gly Gly Ile Gly
    1025            1030            1035

Val Leu Thr Pro Asp Asn Tyr Leu Ile Thr Pro Ala Leu Asp Leu
    1040            1045            1050

Pro Asn Gly Gly Lys Leu Thr Phe Trp Val Cys Ala Gln Asp Ala
    1055            1060            1065

Asn Tyr Ala Ser Glu His Tyr Ala Val Tyr Ala Ser Ser Thr Gly
    1070            1075            1080

Asn Asp Ala Ser Asn Phe Thr Asn Ala Leu Leu Glu Glu Thr Ile
    1085            1090            1095

Thr Ala Lys Gly Val Arg Ser Pro Lys Ala Ile Arg Gly Arg Ile
    1100            1105            1110

Gln Gly Thr Trp Arg Gln Lys Thr Val Asp Leu Pro Ala Gly Thr
    1115            1120            1125

Lys Tyr Val Ala Phe Arg His Phe Gln Ser Thr Asp Met Phe Tyr
    1130            1135            1140

Ile Asp Leu Asp Glu Val Glu Ile Lys Ala Asn Gly Lys Arg Ala
    1145            1150            1155

Asp Phe Thr Glu Thr Phe Glu Ser Ser Thr His Gly Glu Ala Pro
    1160            1165            1170

Ala Glu Trp Thr Thr Ile Asp Ala Asp Gly Asp Gly Gln Gly Trp
    1175            1180            1185

Leu Cys Leu Ser Ser Gly Gln Leu Asp Trp Leu Thr Ala His Gly
    1190            1195            1200

Gly Ser Asn Val Val Ser Ser Phe Ser Trp Asn Gly Met Ala Leu
    1205            1210            1215

Asn Pro Asp Asn Tyr Leu Ile Ser Lys Asp Val Thr Gly Ala Thr
    1220            1225            1230

Lys Val Lys Tyr Tyr Tyr Ala Val Asn Asp Gly Phe Pro Gly Asp
    1235            1240            1245

His Tyr Ala Val Met Ile Ser Lys Thr Gly Thr Asn Ala Gly Asp
    1250            1255            1260

Phe Thr Val Val Phe Glu Glu Thr Pro Asn Gly Ile Asn Lys Gly
    1265            1270            1275

Gly Ala Arg Phe Gly Leu Ser Thr Glu Ala Asn Gly Ala Lys Pro
    1280            1285            1290

Gln Ser Val Trp Ile Glu Arg Thr Val Asp Leu Pro Ala Gly Thr
    1295            1300            1305

Lys Tyr Val Ala Phe Arg His Tyr Asn Cys Ser Asp Leu Asn Tyr
    1310            1315            1320

Ile Leu Leu Asp Asp Ile Gln Phe Thr Met Gly Gly Ser Pro Thr
    1325            1330            1335
```

-continued

Pro Thr Asp Tyr Thr Tyr Val Tyr Arg Asp Gly Thr Lys Ile
            1340            1345            1350

Lys Glu Gly Leu Thr Glu Thr Thr Phe Glu Glu Asp Gly Val Ala
            1355            1360            1365

Thr Gly Asn His Glu Tyr Cys Val Glu Val Lys Tyr Thr Ala Gly
            1370            1375            1380

Val Ser Pro Lys Lys Cys Val Asn Val Thr Val Asn Ser Thr Gln
            1385            1390            1395

Phe Asn Pro Val Gln Asn Leu Thr Ala Glu Gln Ala Pro Asn Ser
            1400            1405            1410

Met Asp Ala Ile Leu Lys Trp Asn Ala Pro Ala Ser Lys Arg Ala
            1415            1420            1425

Glu Val Leu Asn Glu Asp Phe Glu Asn Gly Ile Pro Ala Ser Trp
            1430            1435            1440

Lys Thr Ile Asp Ala Asp Gly Asp Gly Asn Asn Trp Thr Thr Thr
            1445            1450            1455

Pro Pro Pro Gly Gly Ser Ser Phe Ala Gly His Asn Ser Ala Ile
            1460            1465            1470

Cys Val Ser Ser Ala Ser Tyr Ile Asn Phe Glu Gly Pro Gln Asn
            1475            1480            1485

Pro Asp Asn Tyr Leu Val Thr Pro Glu Leu Ser Leu Pro Gly Gly
            1490            1495            1500

Gly Thr Leu Thr Phe Trp Val Cys Ala Gln Asp Ala Asn Tyr Ala
            1505            1510            1515

Ser Glu His Tyr Ala Val Tyr Ala Ser Ser Thr Gly Asn Asp Ala
            1520            1525            1530

Ser Asn Phe Ala Asn Ala Leu Leu Glu Glu Val Leu Thr Ala Lys
            1535            1540            1545

Thr Val Val Thr Ala Pro Glu Ala Ile Arg Gly Thr Arg Ala Gln
            1550            1555            1560

Gly Thr Trp Tyr Gln Lys Thr Val Gln Leu Pro Ala Gly Thr Lys
            1565            1570            1575

Tyr Val Ala Phe Arg His Phe Gly Cys Thr Asp Phe Phe Trp Ile
            1580            1585            1590

Asn Leu Asp Asp Val Val Ile Thr Ser Gly Asn Ala Pro Ser Tyr
            1595            1600            1605

Thr Tyr Thr Ile Tyr Arg Asn Asn Thr Gln Ile Ala Ser Gly Val
            1610            1615            1620

Thr Glu Thr Thr Tyr Arg Asp Pro Asp Leu Ala Thr Gly Phe Tyr
            1625            1630            1635

Thr Tyr Gly Val Lys Val Val Tyr Pro Asn Gly Glu Ser Ala Ile
            1640            1645            1650

Glu Thr Ala Thr Leu Asn Ile Thr Ser Leu Ala Asp Val Thr Ala
            1655            1660            1665

Gln Lys Pro Tyr Thr Leu Thr Val Val Gly Lys Thr Ile Thr Val
            1670            1675            1680

Thr Cys Gln Gly Glu Ala Met Ile Tyr Asp Met Asn Gly Arg Arg
            1685            1690            1695

Leu Ala Ala Gly Arg Asn Thr Val Val Tyr Thr Ala Gln Gly Gly
            1700            1705            1710

His Tyr Ala Val Met Val Val Asp Gly Lys Ser Tyr Val Glu
            1715            1720            1725

Lys Leu Ala Val Lys
     1730

<210> SEQ ID NO 2
<211> LENGTH: 509
<212> TYPE: PRT
<213> ORGANISM: Porphyromonas gingivalis

<400> SEQUENCE: 2

Asp Val Tyr Thr Asp His Gly Asp Leu Tyr Asn Thr Pro Val Arg Met
1               5                   10                  15

Leu Val Val Ala Gly Ala Lys Phe Lys Glu Ala Leu Lys Pro Trp Leu
            20                  25                  30

Thr Trp Lys Ala Gln Lys Gly Phe Tyr Leu Asp Val His Tyr Thr Asp
        35                  40                  45

Glu Ala Glu Val Gly Thr Thr Asn Ala Ser Ile Lys Ala Phe Ile His
    50                  55                  60

Lys Lys Tyr Asn Asp Gly Leu Ala Ala Ser Ala Ala Pro Val Phe Leu
65                  70                  75                  80

Ala Leu Val Gly Asp Thr Asp Val Ile Ser Gly Glu Lys Gly Lys Lys
                85                  90                  95

Thr Lys Lys Val Thr Asp Leu Tyr Tyr Ser Ala Val Asp Gly Asp Tyr
            100                 105                 110

Phe Pro Glu Met Tyr Thr Phe Arg Met Ser Ala Ser Pro Glu Glu
        115                 120                 125

Leu Thr Asn Ile Ile Asp Lys Val Leu Met Tyr Glu Lys Ala Thr Met
    130                 135                 140

Pro Asp Lys Ser Tyr Leu Glu Lys Val Leu Leu Ile Ala Gly Ala Asp
145                 150                 155                 160

Tyr Ser Trp Asn Ser Gln Val Gly Gln Pro Thr Ile Lys Tyr Gly Met
                165                 170                 175

Gln Tyr Tyr Tyr Asn Gln Glu His Gly Tyr Thr Asp Val Tyr Asn Tyr
            180                 185                 190

Leu Lys Ala Pro Tyr Thr Gly Cys Tyr Ser His Leu Asn Thr Gly Val
        195                 200                 205

Ser Phe Ala Asn Tyr Thr Ala His Gly Ser Glu Thr Ala Trp Ala Asp
    210                 215                 220

Pro Leu Leu Thr Thr Ser Gln Leu Lys Ala Leu Thr Asn Lys Asp Lys
225                 230                 235                 240

Tyr Phe Leu Ala Ile Gly Asn Cys Cys Ile Thr Ala Gln Phe Asp Tyr
                245                 250                 255

Val Gln Pro Cys Phe Gly Glu Val Ile Thr Arg Val Lys Glu Lys Gly
            260                 265                 270

Ala Tyr Ala Tyr Ile Gly Ser Ser Pro Asn Ser Tyr Trp Gly Glu Asp
        275                 280                 285

Tyr Tyr Trp Ser Val Gly Ala Asn Ala Val Phe Gly Val Gln Pro Thr
    290                 295                 300

Phe Glu Gly Thr Ser Met Gly Ser Tyr Asp Ala Thr Phe Leu Glu Asp
305                 310                 315                 320

Ser Tyr Asn Thr Val Asn Ser Ile Met Trp Ala Gly Asn Leu Ala Ala
                325                 330                 335

Thr His Ala Gly Asn Ile Gly Asn Ile Thr His Ile Gly Ala His Tyr
            340                 345                 350

Tyr Trp Glu Ala Tyr His Val Leu Gly Asp Gly Ser Val Met Pro Tyr
        355                 360                 365

```
Arg Ala Met Pro Lys Thr Asn Thr Tyr Thr Leu Pro Ala Ser Leu Pro
    370                 375                 380

Gln Asn Gln Ala Ser Tyr Ser Ile Gln Ala Ser Ala Gly Ser Tyr Val
385                 390                 395                 400

Ala Ile Ser Lys Asp Gly Val Leu Tyr Gly Thr Gly Val Ala Asn Ala
                405                 410                 415

Ser Gly Val Ala Thr Val Ser Met Thr Lys Gln Ile Thr Glu Asn Gly
                420                 425                 430

Asn Tyr Asp Val Val Ile Thr Arg Ser Asn Tyr Leu Pro Val Ile Lys
            435                 440                 445

Gln Ile Gln Val Gly Glu Pro Ser Pro Tyr Gln Pro Val Ser Asn Leu
450                 455                 460

Thr Ala Thr Thr Gln Gly Gln Lys Val Thr Leu Lys Trp Glu Ala Pro
465                 470                 475                 480

Ser Ala Lys Lys Ala Glu Gly Ser Arg Glu Val Lys Arg Ile Gly Asp
                485                 490                 495

Gly Leu Phe Val Thr Ile Glu Pro Ala Asn Asp Val Arg
                500                 505

<210> SEQ ID NO 3
<211> LENGTH: 489
<212> TYPE: PRT
<213> ORGANISM: Porphyromonas gingivalis

<400> SEQUENCE: 3

Asp Val Tyr Thr Asp His Gly Asp Leu Tyr Asn Thr Pro Val Arg Met
1               5                   10                  15

Leu Val Val Ala Gly Ala Lys Phe Lys Glu Ala Leu Lys Pro Trp Leu
                20                  25                  30

Thr Trp Lys Ala Gln Lys Gly Phe Tyr Leu Asp Val His Tyr Thr Asp
            35                  40                  45

Glu Ala Glu Val Gly Thr Thr Asn Ala Ser Ile Lys Ala Phe Ile His
    50                  55                  60

Lys Lys Tyr Asn Asp Gly Leu Ala Ala Ser Ala Ala Pro Val Phe Leu
65              70                  75                  80

Ala Leu Val Gly Asp Thr Asp Val Ile Ser Gly Glu Lys Gly Lys Lys
                85                  90                  95

Thr Lys Lys Val Thr Asp Leu Tyr Tyr Ser Ala Val Asp Gly Asp Tyr
            100                 105                 110

Phe Pro Glu Met Tyr Thr Phe Arg Met Ser Ala Ser Ser Pro Glu Glu
        115                 120                 125

Leu Thr Asn Ile Ile Asp Lys Val Leu Met Tyr Glu Lys Ala Thr Met
130                 135                 140

Pro Asp Lys Ser Tyr Leu Glu Lys Val Leu Leu Ile Ala Gly Ala Asp
145                 150                 155                 160

Tyr Ser Trp Asn Ser Gln Val Gly Gln Pro Thr Ile Lys Tyr Gly Met
                165                 170                 175

Gln Tyr Tyr Tyr Asn Gln Glu His Gly Tyr Thr Asp Val Tyr Asn Tyr
            180                 185                 190

Leu Lys Ala Pro Tyr Thr Gly Cys Tyr Ser His Leu Asn Thr Gly Val
        195                 200                 205

Ser Phe Ala Asn Tyr Thr Ala His Gly Ser Glu Thr Ala Trp Ala Asp
210                 215                 220

Pro Leu Leu Thr Thr Ser Gln Leu Lys Ala Leu Thr Asn Lys Asp Lys
```

```
                225                 230                 235                 240

Tyr Phe Leu Ala Ile Gly Asn Cys Cys Ile Thr Ala Gln Phe Asp Tyr
            245                 250                 255

Val Gln Pro Cys Phe Gly Glu Val Ile Thr Arg Val Lys Glu Lys Gly
            260                 265                 270

Ala Tyr Ala Tyr Ile Gly Ser Ser Pro Asn Ser Tyr Trp Gly Glu Asp
            275                 280                 285

Tyr Tyr Trp Ser Val Gly Ala Asn Ala Val Phe Gly Val Gln Pro Thr
            290                 295                 300

Phe Glu Gly Thr Ser Met Gly Ser Tyr Asp Ala Thr Phe Leu Glu Asp
305                 310                 315                 320

Ser Tyr Asn Thr Val Asn Ser Ile Met Trp Ala Gly Asn Leu Ala Ala
                325                 330                 335

Thr His Ala Gly Asn Ile Gly Asn Ile Thr His Ile Gly Ala His Tyr
                340                 345                 350

Tyr Trp Glu Ala Tyr His Val Leu Gly Asp Gly Ser Val Met Pro Tyr
            355                 360                 365

Arg Ala Met Pro Lys Thr Asn Thr Tyr Thr Leu Pro Ala Ser Leu Pro
    370                 375                 380

Gln Asn Gln Ala Ser Tyr Ser Ile Gln Ala Ser Ala Gly Ser Tyr Val
385                 390                 395                 400

Ala Ile Ser Lys Asp Gly Val Leu Tyr Gly Thr Gly Val Ala Asn Ala
                405                 410                 415

Ser Gly Val Ala Thr Val Ser Met Thr Lys Gln Ile Thr Glu Asn Gly
            420                 425                 430

Asn Tyr Asp Val Val Ile Thr Arg Ser Asn Tyr Leu Pro Val Ile Lys
            435                 440                 445

Gln Ile Gln Val Gly Glu Pro Ser Pro Tyr Gln Pro Val Ser Asn Leu
        450                 455                 460

Thr Ala Thr Thr Gln Gly Gln Lys Val Thr Leu Lys Trp Glu Ala Pro
465                 470                 475                 480

Ser Ala Lys Lys Ala Glu Gly Ser Arg
                485

<210> SEQ ID NO 4
<211> LENGTH: 372
<212> TYPE: PRT
<213> ORGANISM: Porphyromonas gingivalis

<400> SEQUENCE: 4

Asp Val Tyr Thr Asp His Gly Asp Leu Tyr Asn Thr Pro Val Arg Met
1               5                   10                  15

Leu Val Val Ala Gly Ala Lys Phe Lys Glu Ala Leu Lys Pro Trp Leu
            20                  25                  30

Thr Trp Lys Ala Gln Lys Gly Phe Tyr Leu Asp Val His Tyr Thr Asp
        35                  40                  45

Glu Ala Glu Val Gly Thr Thr Asn Ala Ser Ile Lys Ala Phe Ile His
    50                  55                  60

Lys Lys Tyr Asn Asp Gly Leu Ala Ala Ser Ala Ala Pro Val Phe Leu
65                  70                  75                  80

Ala Leu Val Gly Asp Thr Asp Val Ile Ser Gly Glu Lys Gly Lys Lys
                85                  90                  95

Thr Lys Lys Val Thr Asp Leu Tyr Tyr Ser Ala Val Asp Gly Asp Tyr
            100                 105                 110
```

Phe Pro Glu Met Tyr Thr Phe Arg Met Ser Ala Ser Ser Pro Glu Glu
            115                 120                 125

Leu Thr Asn Ile Ile Asp Lys Val Leu Met Tyr Glu Lys Ala Thr Met
    130                 135                 140

Pro Asp Lys Ser Tyr Leu Glu Lys Val Leu Leu Ile Ala Gly Ala Asp
145                 150                 155                 160

Tyr Ser Trp Asn Ser Gln Val Gly Gln Pro Thr Ile Lys Tyr Gly Met
                165                 170                 175

Gln Tyr Tyr Tyr Asn Gln Glu His Gly Tyr Thr Asp Val Tyr Asn Tyr
            180                 185                 190

Leu Lys Ala Pro Tyr Thr Gly Cys Tyr Ser His Leu Asn Thr Gly Val
        195                 200                 205

Ser Phe Ala Asn Tyr Thr Ala His Gly Ser Glu Thr Ala Trp Ala Asp
    210                 215                 220

Pro Leu Leu Thr Thr Ser Gln Leu Lys Ala Leu Thr Asn Lys Asp Lys
225                 230                 235                 240

Tyr Phe Leu Ala Ile Gly Asn Cys Cys Ile Thr Ala Gln Phe Asp Tyr
                245                 250                 255

Val Gln Pro Cys Phe Gly Glu Val Ile Thr Arg Val Lys Glu Lys Gly
            260                 265                 270

Ala Tyr Ala Tyr Ile Gly Ser Ser Pro Asn Ser Tyr Trp Gly Glu Asp
        275                 280                 285

Tyr Tyr Trp Ser Val Gly Ala Asn Ala Val Phe Gly Val Gln Pro Thr
    290                 295                 300

Phe Glu Gly Thr Ser Met Gly Ser Tyr Asp Ala Thr Phe Leu Glu Asp
305                 310                 315                 320

Ser Tyr Asn Thr Val Asn Ser Ile Met Trp Ala Gly Asn Leu Ala Ala
                325                 330                 335

Thr His Ala Gly Asn Ile Gly Asn Ile Thr His Ile Gly Ala His Tyr
            340                 345                 350

Tyr Trp Glu Ala Tyr His Val Leu Gly Asp Gly Ser Val Met Pro Tyr
        355                 360                 365

Arg Ala Met Pro
    370

<210> SEQ ID NO 5
<211> LENGTH: 21
<212> TYPE: PRT
<213> ORGANISM: Homo sapiens

<400> SEQUENCE: 5

Asp Lys Thr His Thr Cys Pro Pro Cys Pro Ala Pro Glu Leu Leu Gly
1               5                   10                  15

Gly Pro Ser Val Phe
            20

<210> SEQ ID NO 6
<211> LENGTH: 2
<212> TYPE: PRT
<213> ORGANISM: Artificial Sequence
<220> FEATURE:
<223> OTHER INFORMATION: hinge fragment 1

<400> SEQUENCE: 6

Asp Lys
1

```
<210> SEQ ID NO 7
<211> LENGTH: 19
<212> TYPE: PRT
<213> ORGANISM: Artificial Sequence
<220> FEATURE:
<223> OTHER INFORMATION: hinge fragment 2

<400> SEQUENCE: 7

Thr His Thr Cys Pro Pro Cys Pro Ala Pro Glu Leu Leu Gly Gly Pro
1               5                   10                  15

Ser Val Phe
```